US011850246B2

(12) United States Patent
Lee et al.

(10) Patent No.: US 11,850,246 B2
(45) Date of Patent: Dec. 26, 2023

(54) METHOD FOR TREATMENT OF CYTOKINE RELEASE SYNDROME

(71) Applicant: NOVMETAPHARMA CO., LTD., Seoul (KR)

(72) Inventors: In-Kyu Lee, Daegu (KR); Jae-Han Jeon, Daegu (KR); Dipanjan Chanda, Daegu (KR); Eun Jung Choi, Daegu (KR); Hoe-Yune Jung, Pohang (KR); Heon Jong Lee, Incheon (KR)

(73) Assignee: NOVMETAPHARMA CO., LTD., Seoul (KR)

( * ) Notice: Subject to any disclaimer, the term of this patent is extended or adjusted under 35 U.S.C. 154(b) by 50 days.

(21) Appl. No.: 17/393,587

(22) Filed: Aug. 4, 2021

(65) Prior Publication Data

US 2022/0040171 A1     Feb. 10, 2022

Related U.S. Application Data

(60) Provisional application No. 63/060,779, filed on Aug. 4, 2020.

(51) Int. Cl.
*A61K 31/495* (2006.01)
*A61P 29/00* (2006.01)

(52) U.S. Cl.
CPC .................................. *A61K 31/495* (2013.01)

(58) Field of Classification Search
CPC .............................. A61K 31/495; A61P 29/00
See application file for complete search history.

(56) References Cited

U.S. PATENT DOCUMENTS

| 2008/0255089 A1 | 10/2008 | Katamreddy |
| 2013/0231333 A1 | 9/2013 | Smith et al. |
| 2020/0079805 A1 | 3/2020 | Hubackova et al. |

FOREIGN PATENT DOCUMENTS

| KR | 10-2015-0035432 A | 4/2015 |
| KR | 10-2018-0001240 A | 1/2018 |
| WO | 92/06068 A1 | 4/1992 |
| WO | 01/36360 A1 | 5/2001 |

OTHER PUBLICATIONS

Shimabukuro-Vornhagen et al. ("Cytokine release syndrome." J Immunother Cancer. Jun. 15, 2018;6(1):56. doi:10.1186/s40425-018-0343-9. PMID: 29907163; PMCID: PMC6003181.) (Year: 2018).*
J. G. Cannon Chapter Nineteen in Burger's Medicinal Chemistry and Drug Discovery, Fifth Edition, vol. I: Principles and Practice, Wiley-Interscience 1995, pp. 783-802, 784. (Year: 1995).*
Dick RM (2011). "Chapter 2. Pharmacodynamics: The Study of Drug Action". In Ouellette R, Joyce JA. Pharmacology for Nurse Anesthesiology. Jones & Bartlett Learning:pp. 17-26. (Year: 2011).*
Kim, J. et al., "Insights of a Lead Optimization Study and Biological Evaluation of Novel 4-Hydroxytamoxifen Analogs as Estrogen-Related Receptor γ (ERRγ) Inverse Agonists," Journal of Medicinal Chemistry, Nov. 2, 2016, vol. 59, No. 22, pp. 10209-10227, (20 pages total).
Abdellatif, K. et al., "Design, synthesis and biological evaluation of novel triaryl (Z)-olefins as tamoxifen analogues," Bioorganic & Medicinal Chemistry Letters, vol. 23, No. 17, Sep. 1, 2013, Published Online Jun. 26, 2013, pp. 4960-4963 (5 pages total).
Singh, T. et al., "Inverse Agonist of Estrogen-Related Receptor γ Enhances Sodium Iodide Symporter Function Through Mitogen-Activated Protein Kinase Signaling in Anaplastic Thyroid Cancer Cells," The Journal of Nuclear Medicine, Nov. 2015, Published Online Sep. 3, 2015, vol. 56, No. 11, pp. 1690-1696, (9 pages total).
Kim, J. et al., "Synthesis and biological evaluation of novel 4-hydroxytamoxifen analogs as estrogen-related receptor gamma inverse agonists," European Journal of Medicine Chemistry, Sep. 14, 2016, Published Online May 9, 2016, vol. 120, pp. 338-352 (16 pages total).
Bouakouk-Chitti et al., "Ligand-based studies on cis-stilbene derivatives as cyclo-oxygenase inhibitors", Medicinal chemistry research, vol. 26, No. 8, pp. 1801-1811, Apr. 17, 2017 (11 pages total).

\* cited by examiner

*Primary Examiner* — Jeffrey S Lundgren
*Assistant Examiner* — Chris E Simmons
(74) *Attorney, Agent, or Firm* — Sughrue Mion, PLLC

(57) ABSTRACT

A composition for preventing and/or treating cytokine release syndrome and a method of prevention and/or treatment of cytokine release syndrome are disclosed. The composition includes an aryl ethene compound, a pharmaceutically acceptable salt thereof, or a solvate thereof, as an active ingredient. The method includes administering the aryl ethene compound, an isomer, a pharmaceutically acceptable salt thereof, or a solvate thereof, in an effective amount to a subject in need thereof. The cytokine release syndrome may be caused by virulent infection. The administration of the compound reduces the pre-inflammatory cytokine levels in the subject.

9 Claims, 2 Drawing Sheets

METHOD FOR TREATMENT OF CYTOKINE RELEASE SYNDROME

CROSS REFERENCE TO RELATED APPLICATION

This application claims priority to and benefits based on U.S. Provisional Patent application No. 63/060,779 filed Aug. 4, 2020, the content of which is incorporated by reference herein in its entirety.

FILED

This disclosure includes a method for treatment of cytokine release syndrome. In an aspect, the disclosure concerns the use of a molecule to reduce or prevent exaggerated production of cytokines in macrophage upon virulent infection. This molecule serves to prevent mitochondrial dysfunction caused by estrogen-related receptors gamma (ERRg)-mediated pro-inflammatory reaction in macrophages. This disclosure is also concerned with methods of treating a mammal suffering from cytokine release syndrome through the administration of this molecule.

BACKGROUND

Inflammatory disorders underlie numerous human diseases characterized by an exaggerated immune response that leads to secretion of large amounts of circulating pro-inflammatory cytokines after infection with virulent pathogens in response to host cell injury or related irritants that activate receptors on immune effector cells including T cells, macrophages, and the like. For example, sepsis that is an extreme immune response to an infection, according to the Centers for Disease Control and Prevention (CDC), happens when an existing infection—such as a skin, lung or urinary tract infection—triggers a "chain reaction" in the body that leads to widespread inflammation. A recent study published in the Lancet estimated that in 2017, 49 million people developed sepsis and 11 million died from the illness. Kempker and Martin, A global accounting of sepsis, The Lancet, Vol. 395, Issue 10219, pp. 168-170, Jan. 18, 2020. A central feature of these infectious disorders is the burst in cytokine release, i.e. cytokine storm, from pro-inflammatory cells including macrophages, lymphocytes, and polymorphonuclear leukocytes (PMNs). Under many conditions, the cytokine storm is exaggerated (hypercytokinemia) and results in a fatal immune reaction with constant activation of immune effector cells that produce sustained and supraphysiologic levels of cytokines including TNFα, IFNb, IL-1b, and IL-6 that leads to severe tissue injury. These proinflammatory cytokines are produced by several different cell types, most importantly immune cells (for example monocytes, macrophages and neutrophils), but also non-immune cells such as fibroblasts, osteoblasts, smooth muscle cells, epithelial cells, and neurons (56). Proinflammatory cytokines contribute to various disorders, notably sepsis, through their release during an inflammatory cytokine cascade.

The nuclear receptor (NR) superfamily represents a large group of ligand dependent transcription factors. The nuclear receptor family is uniquely differently from other classes of receptors in their ability to directly interact with and control the expression of genomic DNA.

As a consequence, nuclear receptors play key roles in both embryonic development and adult metabolic homeostasis. The estrogen-related receptors (ERRs) were the first orphan members of the superfamily of nuclear receptors to be identified, and the subfamily is now known to contain three related isoforms, ERRα (also known as NR3B1, Esrra, ERRa), β (also known as NR3B2, Esrr, ERRb), and γ (also known as NR3B3, Esrrg, ERRg). Although named after the estrogen receptors due to their structural homology, the ERRs are not activated by estrogens (ligand for estrogen receptors) or any known natural compounds. ERRs play an important role in the transcriptional control of metabolic genes involved in the generation and utilization of cellular energy and thus plays a critical role in key facets of organ development as well as cellular homeostasis. ERRs are primarily expressed in the heart, skeletal muscle, brain, kidney, pancreas, placenta, and liver and are predicted to have significant differences in their synthetic ligand binding preferences.

Recent findings in various mammalian experimental models show that ERRg, as a downstream mediator of multiple extracellular signals, plays a key role in coordinating endocrine and metabolic signals, resulting in changes in glucose, alcohol, lipid, and iron metabolism. Therefore, dysregulation of ERRg contributes to the pathogenesis of metabolic diseases such as hyperglycemia, insulin resistance, and alcoholic liver injury. Interestingly, ERRg has been shown to be involved in the pathogenesis of bacterial infection. These findings indicate the importance of ERRg in the endocrine and metabolic control of metabolism, and suggest that ERRg may be a promising therapeutic target for several diseases.

U.S. application Ser. No. 16/313,360 (US Application Publication No. 2019/0167820 A1) and Ser. No. 16/677,596 (Application Publication No. 20200078476 A1), of which entire contents are incorporated herein by reference, disclose novel aryl ethane derivatives as estrogen-related receptor gamma (ERRg) inhibitors.

The disclosure is based on the new finding that certain compounds with ERRg inhibiting activity may be useful in the treatment of virulent infection-induced cytokine release syndrome.

SUMMARY

In general, the present disclosure relates to methods and/or uses for treating, preventing, or managing cytokine release syndrome, which comprises administering an arylethene compound of Chemical Formula (I), an isomer, a prodrug, a pharmaceutically acceptable salt, or a solvate thereof. In one embodiment, cytokine release syndrome is induced by virulent infection. The infection may be an infection by virus or bacteria. The treatment, prevention, or management of cytokine release syndrome may include normalizing pro-inflammatory cytokine level and/or diminishing supraphysiological level of pro-inflammatory cytokine in a patient. The pro-inflammatory cytokine includes, among others, IFNb, IL1b, TNFα, and/or IL6.

The disclosure is directed to a method for preventing, treating, or managing cytokine release syndrome in a subject in need thereof, comprising administering to the subject an aryethene compound of the following Chemical Formula 1:

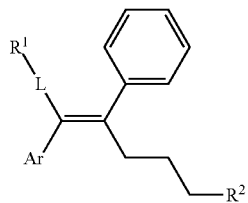

Chemical Formula 1 wherein

L is (C6-C20)arylene, (C3-C20)heteroarylene, or (C3-C20) fused heterocycle;

$R^1$ is (C3-C20)heterocycloalkyl, (C3-C20)heteroaryl, —O—$(CH_2)_m$—$R^{11}$, —$(CH_2)_m$—$R^{12}$, —NH—$(CH_2)_m$—$R^{13}$, —NHCO—$(CH_2)_n$—$R^{14}$, or —$SiR^{16}R^{17}$—$(CH_2)_m$—$R^{15}$;

$R^{11}$ to $R^{15}$ are independently of one another (C3-C20) heterocycloalkyl;

$R^{16}$ and $R^{17}$ are independently of each other (C1-C20) alkyl;

m is an integer of 1 to 3; and n is an integer of 0 or 1;

Ar is (C6-C20)aryl or (C3-C20)heteroaryl, in which the aryl or heteroaryl of Ar may be further substituted by one or more selected from the group consisting of hydroxy, halogen, (C1-C20)alkyl, halo(C1-C20)alkyl, (C1-C20)alkoxy, nitro, cyano, —$NR^{21}R^{22}$, (C1-C20)alkylcarbonyloxy, (C1-C20)alkylcarbonylamino, guanidino, —$SO_2$—$R^{23}$, and —$OSO_2$—$R^{24}$;

$R^{21}$ and $R^{22}$ are independently of each other hydrogen, (C1-C20)alkylsulfonyl, or (C3-C20)cycloalkylsulfonyl;

$R^{23}$ and $R^{24}$ are independently of each other (C1-C20)alkyl, halo(C1-C20)alkyl, or (C3-C20)cycloalkyl;

$R^2$ is hydroxy, halogen, (C1-C20)alkylcarbonyloxy, or (C1-C20)alkylsulfonyloxy;

the heterocycloalkyl or heteroaryl of $R^1$ and the heterocycloalkyl of $R^{11}$ to $R^{15}$ may be further substituted by one or more selected from the group consisting of (C1-C20)alkyl, (C3-C20)cycloalkyl, (C2-C20)alkenyl, amidino, (C1-C20)alkoxycarbonyl, hydroxy, hydroxy(C1-C20)alkyl, and di(C1-C20)alkylamino(C1-C20)alkyl; and the heterocycloalkyl and heteroaryl contains one or more heteroatoms selected from the group consisting of N, O and S, and the heterocycloalkyl is a saturated or unsaturated mono-, bi-, or spirocycle having a carbon atom or nitrogen atom in a ring as a binding site, or a solvate, an isomer, or a pharmaceutically acceptable salt thereof.

In an embodiment, the cytokine release syndrome is syndrome caused by exaggerated immune reaction to virulent infection in a host (subject). The treatment, prevention, or management of cytokine release syndrome may include normalizing pro-inflammatory cytokine level and/or diminishing supraphysiological level of pro-inflammatory cytokine in a patient. The pro-inflammatory cytokine includes, among others, IFNb, IL1b, TNFα, and/or IL6.

Another aspect of this disclosure is a method for treating and/or preventing and/or managing cytokine release syndrome in a viral-infected subject, comprising administering a compound of Chemical Formula 2, or a pharmaceutically acceptable salt thereof, or a solvate thereof,

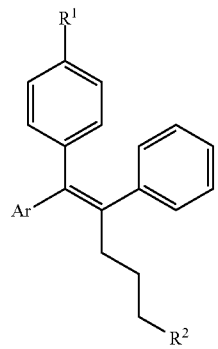

Chemical Formula 2 wherein
$R^1$ is (C3-C10)heterocycloalkyl or —O—$(CH_2)_m$—$R^{11}$;
$R^{11}$ is (C3-C10)heterocycloalkyl;
m is an integer of 1 to 3;
the heterocycloalkyl of $R^1$ and $R^{11}$ may be further substituted by one or more selected from the group consisting of (C1-C10)alkyl, (C3-C10)cycloalkyl, (C2-C10)alkenyl, amidino, (C1-C10)alkoxycarbonyl, hydroxy(C1-C10)alkyl, and di(C1-C20)alkylamino(C1-C20)alkyl;
Ar is (C6-C12)aryl or (C3-C12)heteroaryl, in which the aryl or heteroaryl of Ar may be further substituted by one or more selected from the group consisting of hydroxy, halogen, (C1-C10)alkyl, halo(C1-C10)alkyl, (C1-C10)alkoxy, nitro, cyano, amino, (C1-C10)alkylsulfonylamino, (C3-C10)cycloalkylsulfonylamino, di((C1-C10)alkylsulfonyl)amino, (C1-C10)alkylcarbonyloxy, (C1-C10)alkylcarbonylamino, guanidino, (C1-C10)alkylsulfonyl, (C1-C10)alkylsulfonyloxy, halo(C1-C10)alkylsulfonyloxy, and (C3-C10)cycloalkylsulfonyloxy; and
$R^2$ is hydroxy, fluoro, (C1-C10)alkylcarbonyloxy, or (C1-C10)alkylsulfonyloxy. In an embodiment, the cytokine release syndrome is syndrome caused by exaggerated immune reaction to virulent infection in the subject. In an aspect, the exaggerated immune reaction may be a burst of cytokine release (cytokine storm). Therefore, the treatment, prevention, or management of cytokine release syndrome may include normalizing pro-inflammatory cytokine level and/or diminishing supraphysiological level of pro-inflammatory cytokine in a patient. The pro-inflammatory cytokine includes, among others, IFNb, IL1b, TNFα, and/or IL6.

Another aspect of this disclosure is a method for treating and/or preventing and/or managing cytokine release syndrome in a subject in need thereof, comprising administering a compound of Chemical Formula 6, or a pharmaceutically acceptable salt thereof, or a solvate thereof,

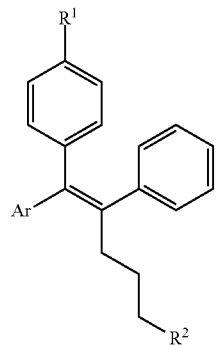

Chemical Formula 6 wherein

R$^1$ is (C3-C10)heterocycloalkyl or —O—(CH2)$_m$-R$^{11}$;

R$^{11}$ is (C3-C10)heterocycloalkyl;

m is an integer of 1 to 3;

Ar is s (C6-C12)aryl or (C3-C12)heteroaryl, wherein the heterocyclalkyl, the aryl, or heteroaryl may be further substituted by one or more selected from the group consisting of hydroxy, halogen, (C1-C10)alkyl, halo (C1-C10)alkyl, (C1-C10)alkoxy, nitro, cyano, amino, (C1-C10)alkylsulfonylamino, (C3-C10)cycloalkylsulfonylamino, di((C1-C10)alkyl sulfonyl)amino, (C1-C10) alkylcarbonyloxy, (C1-C10)alkylcarbonylamino, guanidino, (C1-C10)alkyl sulfonyl, (C1-C10)alkylsulfonyloxy, halo (C1-C10)alkylsulfonyloxy, and (C3-C10)cycloalkylsulfonyloxy; and R$^2$ is hydroxyl, halogen, (C1-C10) alkyl carbonyl oxy, or (C1-C10)alkylsulfonyloxy. In an embodiment, the cytokine release syndrome is syndrome caused by exaggerated immune reaction to virulent infection in the subject. In an aspect, the exaggerated immune reaction may be a burst of cytokine release (cytokine storm). Therefore, the treatment, prevention, or management of cytokine release syndrome may include normalizing pro-inflammatory cytokine level and/or diminishing supraphysiological level of pro-inflammatory cytokine in a patient. The pro-inflammatory cytokine includes, among others, IFNb, IL1b, TNFα, and/or IL6.

According to one embodiment, the compound of Chemical Formula 1 is selected from the following compounds 18a, 18k, 22i, and 22r:

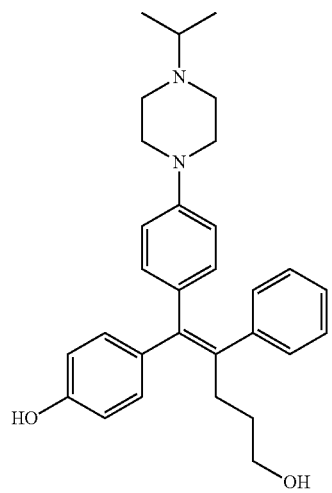

18a

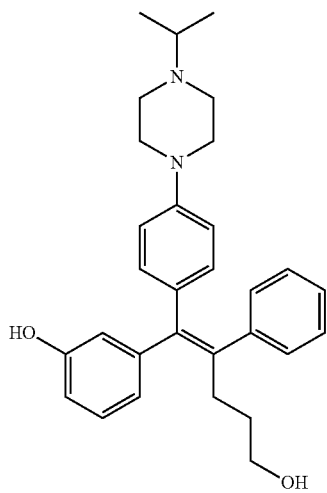

18k

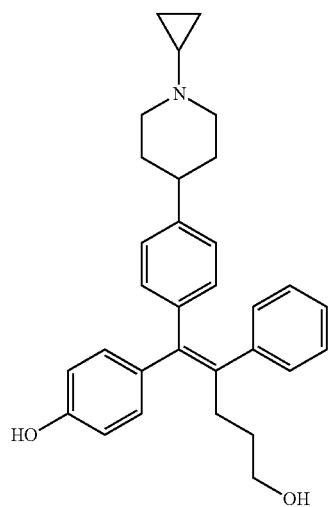

22i

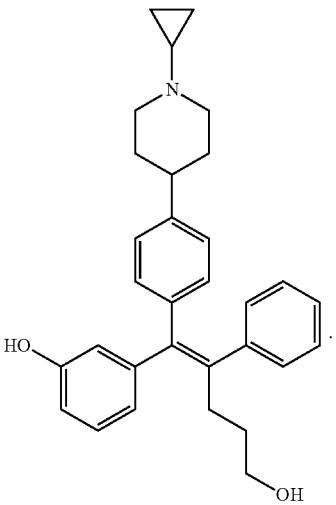

22r

In one aspect, the cytokine release syndrome may be caused by virulent infection. The infection may be an infection by virus or bacteria. The treatment, prevention, or management of cytokine release syndrome may include normalizing pro-inflammatory cytokine level and/or diminishing supraphysiological level of pro-inflammatory cytokine in a patient. The pro-inflammatory cytokine includes, among others, IFNb, IL1b, TNFα, and/or IL6.

In another aspect, the virulent infection-induced cytokine release syndrome may include septic shock, pneumonia, and other inflammatory conditions.

In still another aspect, the subject is a mammal, in particular human.

An aspect of the disclosure is further directed to a pharmaceutical composition for prevention and/or treatment and/or management of cytokine release syndrome, comprising a therapeutically effective amount of a compound of Chemical Formula 1, a solvate, an isomer, or a pharmaceutically acceptable salt thereof, as an active ingredient, and a pharmaceutically acceptable excipient.

An aspect of the disclosure is further directed to a pharmaceutical composition for prevention and/or treatment and/or management of cytokine release syndrome, comprising a therapeutically effective amount of a compound of Chemical Formula 2, a solvate, an isomer, or a pharmaceutically acceptable salt thereof, as an active ingredient, and a pharmaceutically acceptable excipient.

An aspect of the disclosure is further directed to a pharmaceutical composition for prevention and/or treatment and/or management of cytokine release syndrome, comprising a therapeutically effective amount of a compound of Chemical Formula 6, a solvate, an isomer, or a pharmaceutically acceptable salt thereof, as an active ingredient, and a pharmaceutically acceptable excipient.

In the above aspects, the cytokine release syndrome is syndrome caused by exaggerated immune reaction to virulent infection in the subject. In an aspect, the exaggerated immune reaction may be a burst of cytokine release (cytokine storm). The treatment, prevention, or management of cytokine release syndrome may include normalizing pro-inflammatory cytokine level and/or diminishing supraphysiological level of pro-inflammatory cytokine in a patient. The pro-inflammatory cytokine includes, among others, IFNb, IL1b, TNFα, and/or IL6.

In an embodiment, the composition comprises a compound selected from the compounds 18a, 18k, 22i, and 22r, a solvate, an isomer, or a pharmaceutically acceptable salt thereof.

Still another aspect of the disclosure is directed to the use of a compound of Chemical Formula 1, a solvate, an isomer, or a pharmaceutically acceptable salt thereof in the manufacture of a medicament for the prevention and/or treatment and/or management of cytokine release syndrome. In an embodiment, cytokine release syndrome may be caused by virulent infection and may include a burst of cytokine release (cytokine storm). The treatment, prevention, or management of cytokine release syndrome may include normalizing pro-inflammatory cytokine level and/or diminishing supraphysiological level of pro-inflammatory cytokine in a patient. The pro-inflammatory cytokine includes, among others, IFNb, IL1b, TNFα, and/or IL6.

Another aspect of the disclosure is a use of a compound of the Chemical Formula 2 or a pharmaceutically acceptable salt thereof in the manufacture of a medicament for the prevention and/or treatment and/or management of cytokine release syndrome. In an embodiment, the cytokine release syndrome is syndrome caused by exaggerated immune reaction to virulent infection in the subject. In an aspect, the exaggerated immune reaction may be a burst of cytokine release (cytokine storm). Therefore, the treatment, prevention, or management of cytokine release syndrome may include normalizing pro-inflammatory cytokine level and/or diminishing supraphysiological level of pro-inflammatory cytokine in a patient. The pro-inflammatory cytokine includes, among others, IFNb, IL1b, TNFα, and/or IL6.

Another aspect of the disclosure is a use of a compound of the Chemical Formula 6 or a pharmaceutically acceptable salt thereof in the manufacture of a medicament for the prevention and/or treatment and/or management of cytokine release syndrome. In an embodiment, the cytokine release syndrome is syndrome caused by exaggerated immune reaction to virulent infection in the subject. In an aspect, the exaggerated immune reaction may be a burst of cytokine release (cytokine storm). Therefore, the treatment, prevention, or management of cytokine release syndrome may include normalizing pro-inflammatory cytokine level and/or diminishing supraphysiological level of pro-inflammatory cytokine in a patient. The pro-inflammatory cytokine includes, among others, IFNb, IL1b, TNFα, and/or IL6.

Still another aspect of the embodiment is a use of a compound 18a, 18k, 22i, or 22r, or a pharmaceutically acceptable salt thereof, or a solvate, or an isomer thereof, in the manufacture of a medicament for the prevention and/or treatment of cytokine release syndrome. In an embodiment, the cytokine release syndrome is syndrome caused by exaggerated immune reaction to virulent infection in the subject. In an aspect, the exaggerated immune reaction may be a burst of cytokine release (cytokine storm). The treatment, prevention, or management of cytokine release syndrome may include normalizing pro-inflammatory cytokine level and/or diminishing supraphysiological level of pro-inflammatory cytokine in a patient. The pro-inflammatory cytokine includes, among others, IFNb, IL1b, TNFα, and/or IL6.

DETAILED DESCRIPTION OF EMBODIMENTS

Figure 1A:
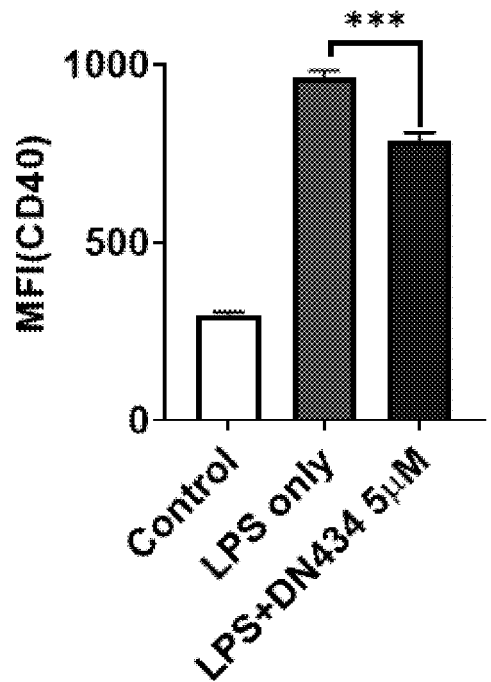
FIGS. 1A-1C show anti-inflammatory effects of a compound of Chemical Formula 1 by suppressing expression of inflammatory surface markers (CD40, CD80, CD86) of macrophage treated with LPS.

The disclosure is directed to a method for preventing and/or treating cytokine release syndrome, comprising administering an arylethene compound of Chemical Formula 1:

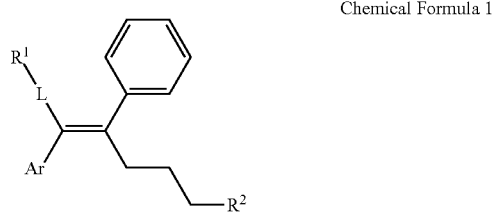

Chemical Formula 1 wherein all the symbols have the same meanings as defined above in Chemical Formula 1, or a solvate, an isomer, or a pharmaceutically acceptable salt thereof.

According to an embodiment, the compound can be a compound of the following Chemical Formula 2:

Chemical Formula 2

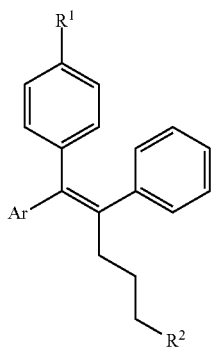

wherein, all the symbols have the same meanings as defined above in Chemical Formula 2, or a solvate, an isomer, or a pharmaceutically acceptable salt thereof.

According to an embodiment, the compound can be a compound of the following Chemical Formula 6:

Chemical Formula 6

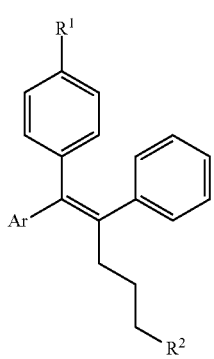

wherein all the symbols have the same meanings as defined above in Chemical Formula 6, a pharmaceutically acceptable salt thereof or a solvate thereof.

According to another embodiment, the compound of Chemical Formula 1 can be one selected from the following compounds:

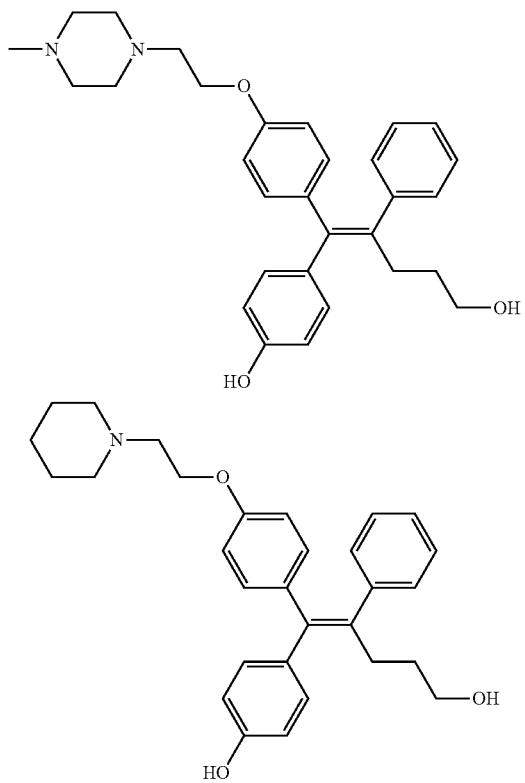

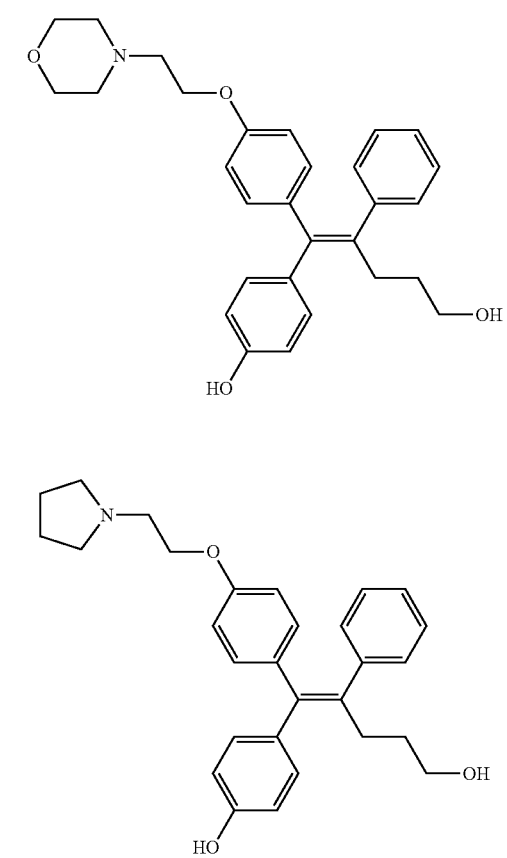

11
-continued
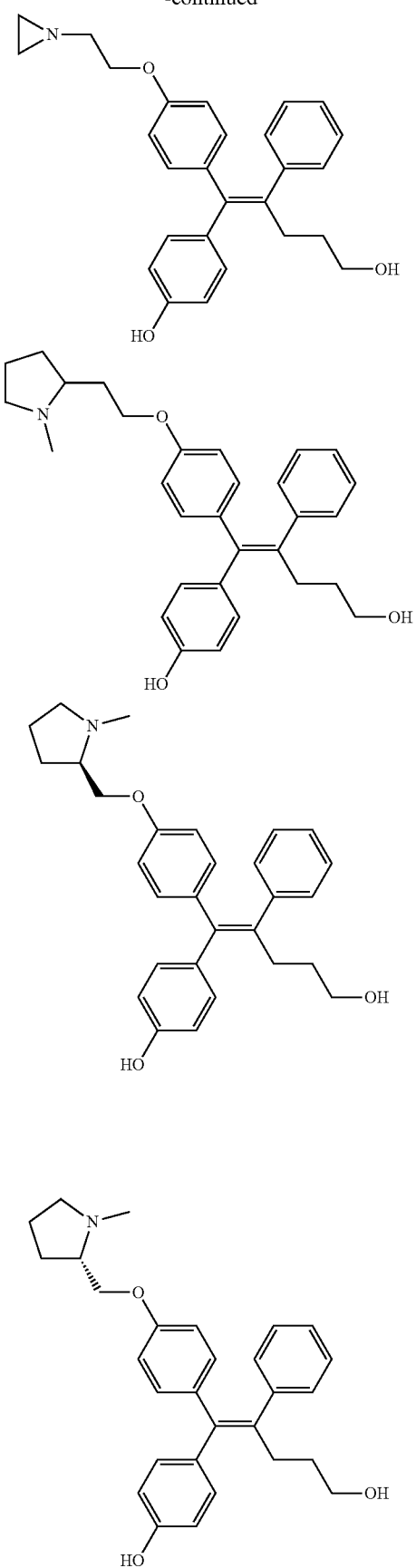
12
-continued
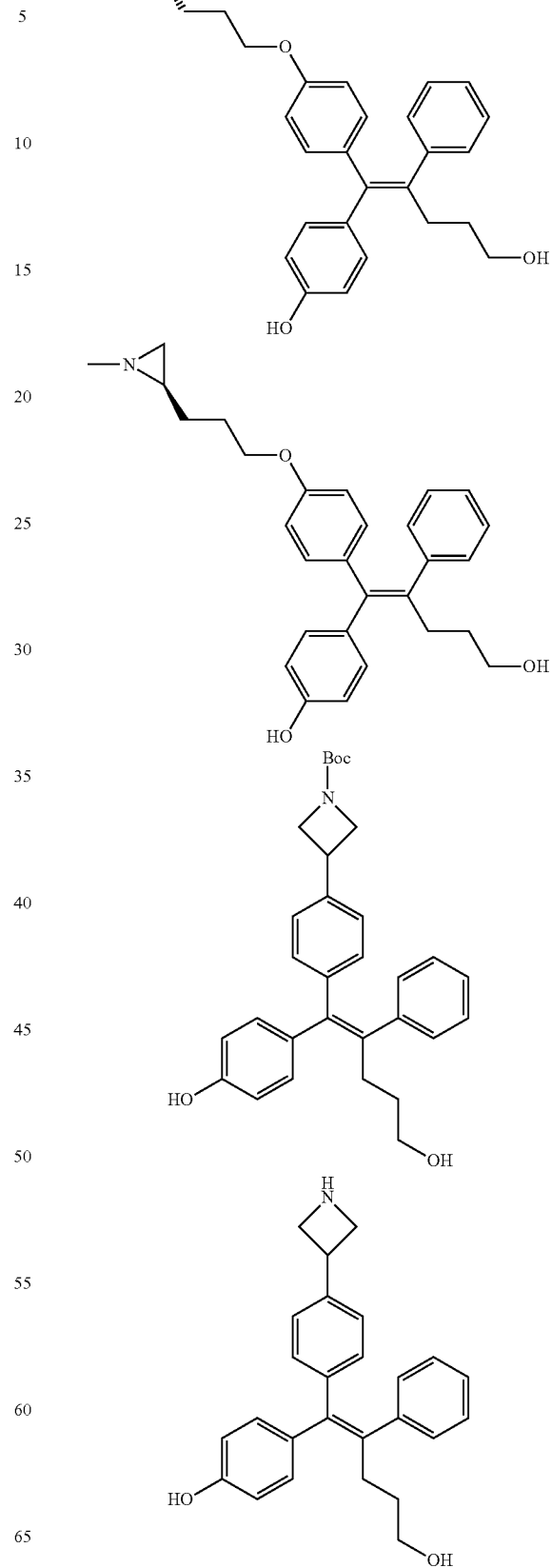

13
-continued
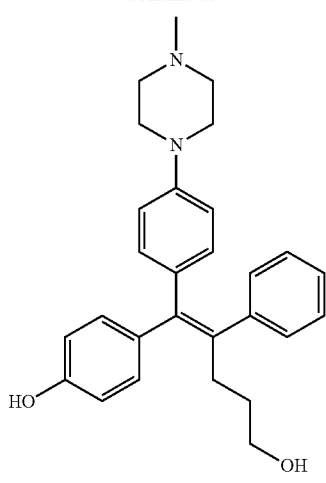
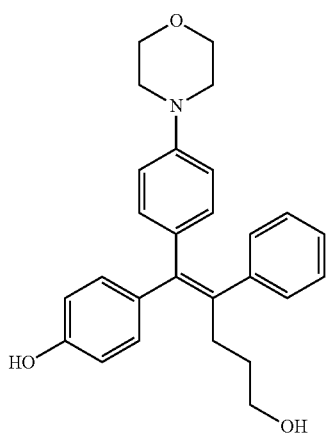
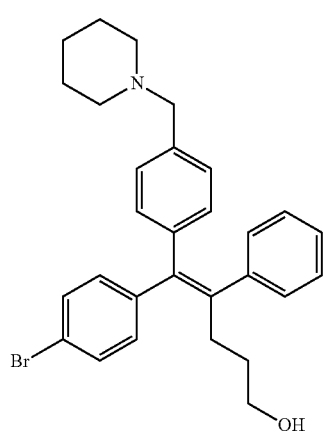
14
-continued
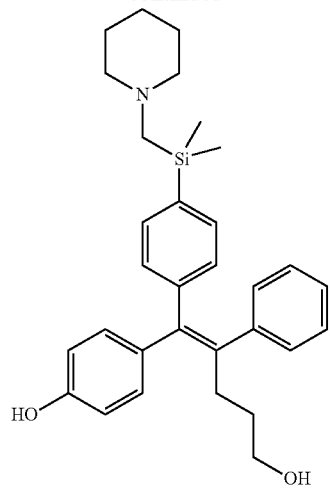
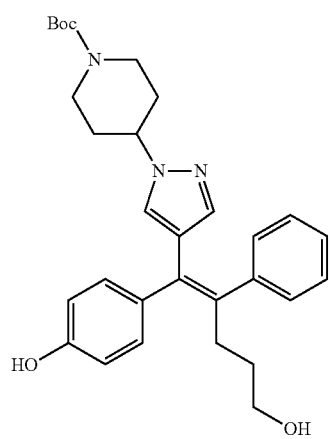
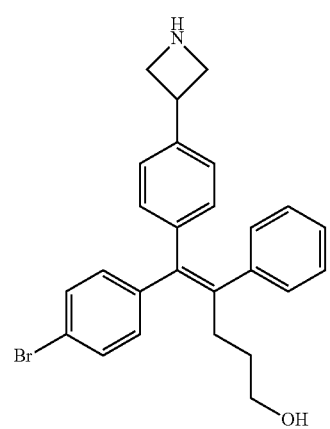

15
-continued
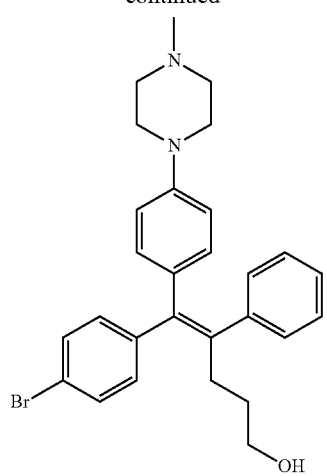
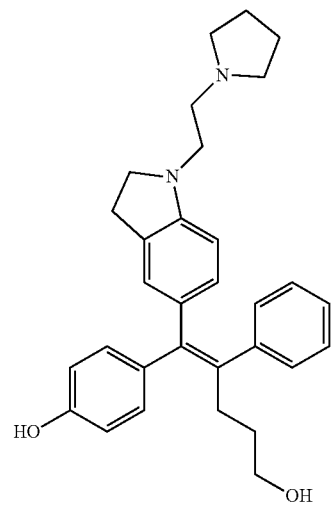
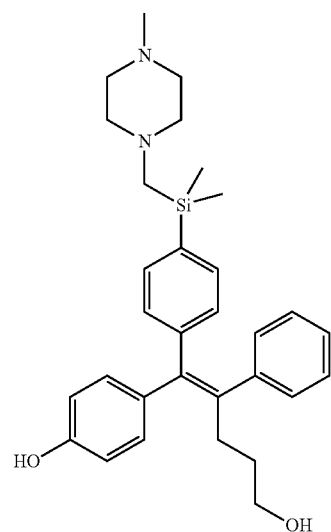
16
-continued
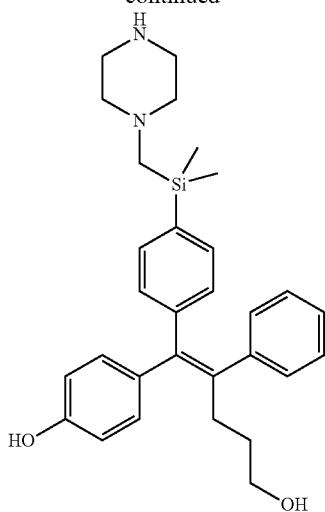
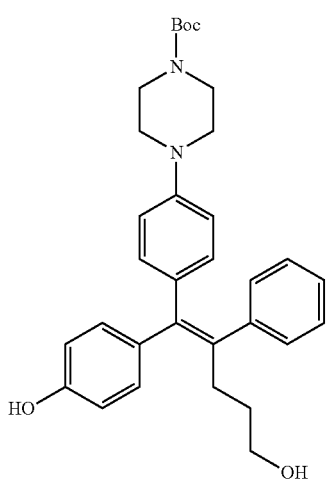
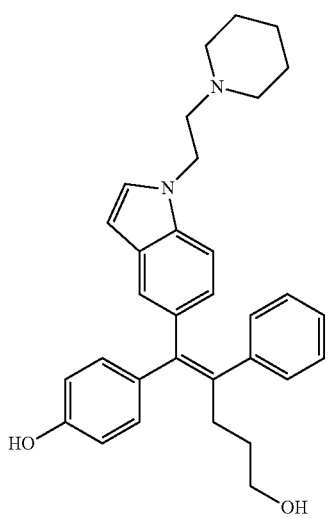

17
-continued
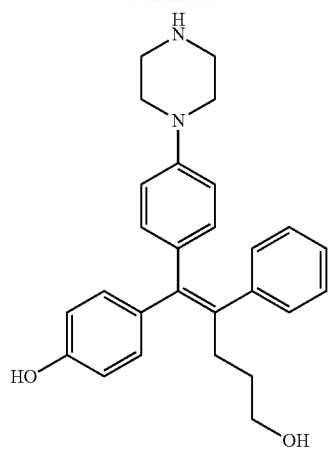
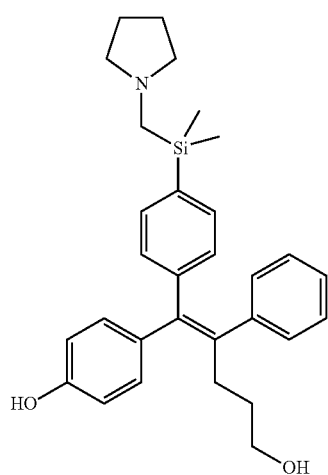
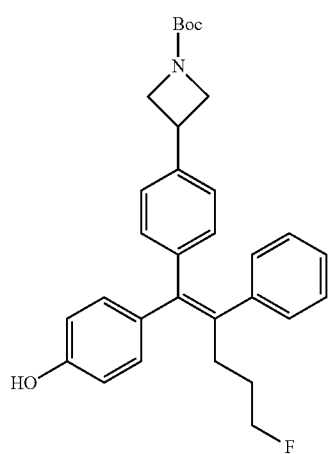
18
-continued
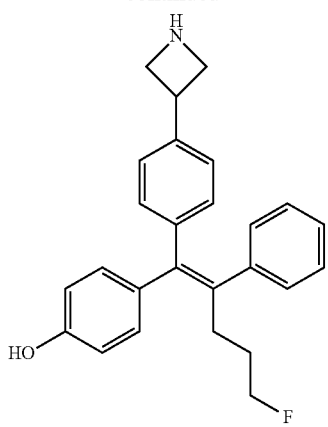
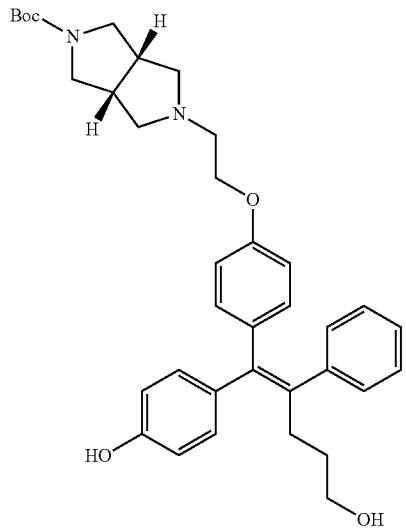
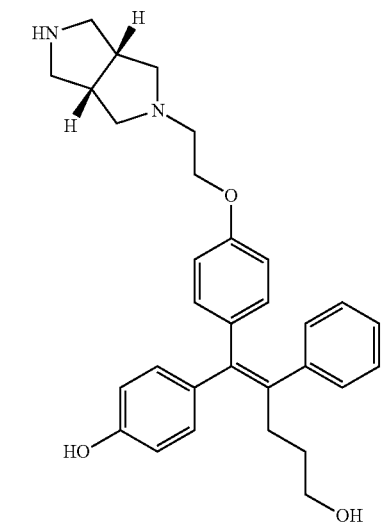

19
-continued
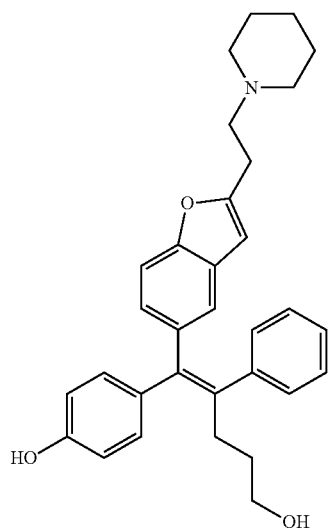
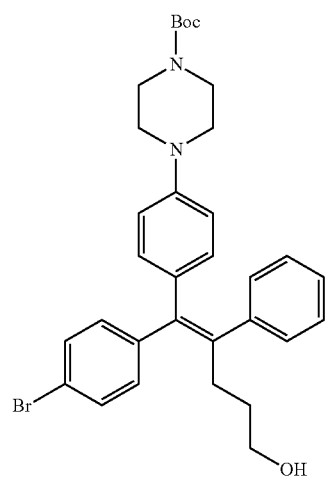
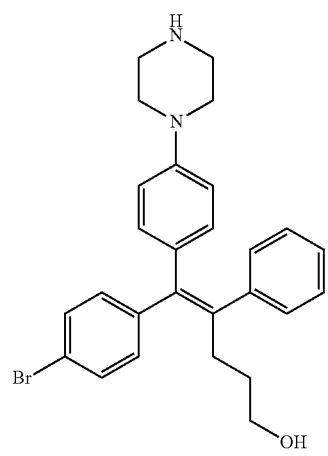
20
-continued
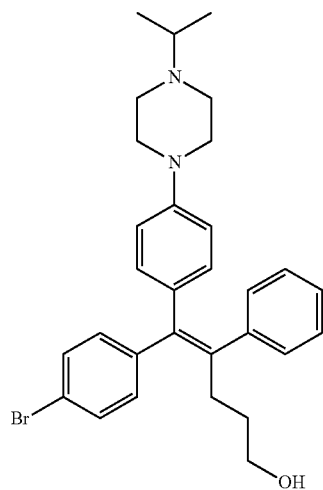
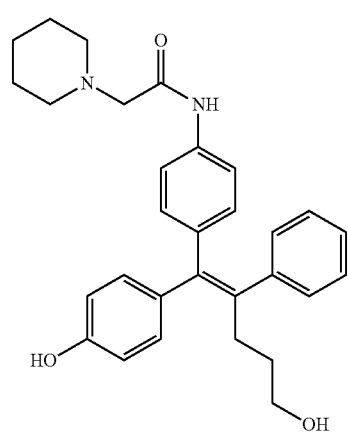
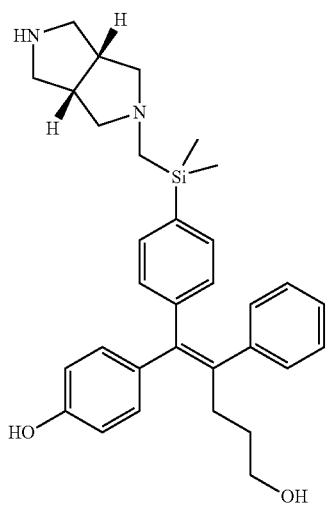

21
-continued
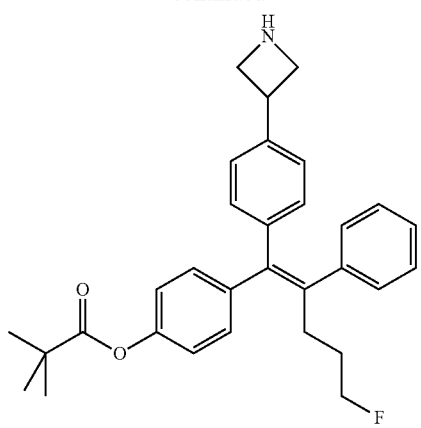
22
-continued
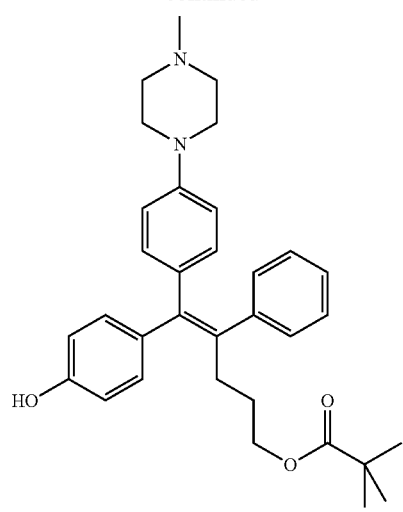
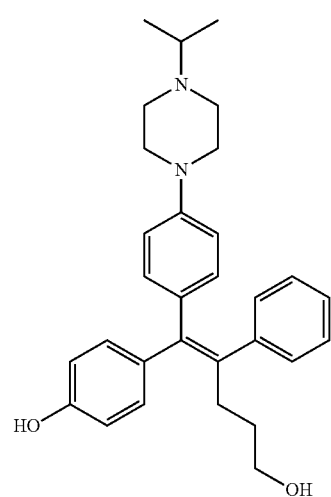
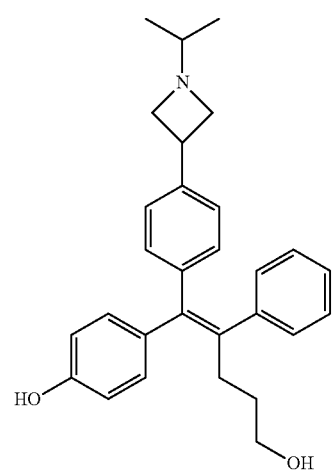
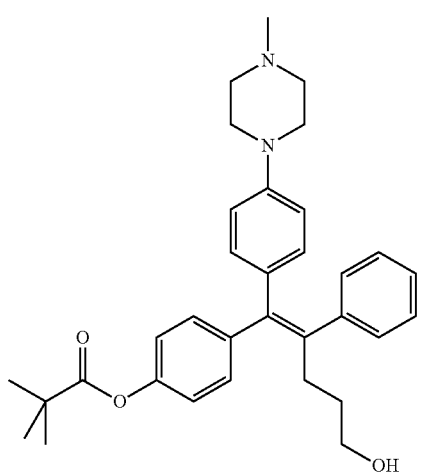
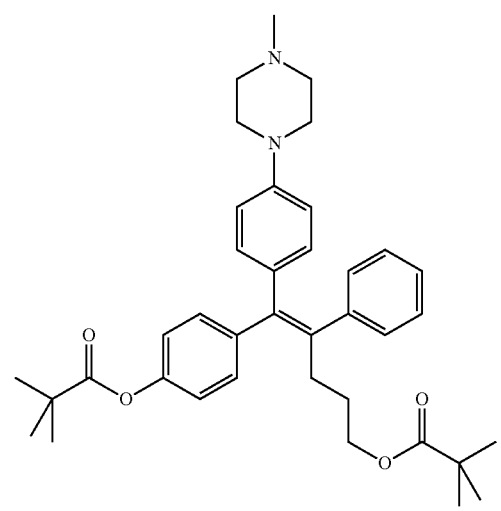

23
-continued
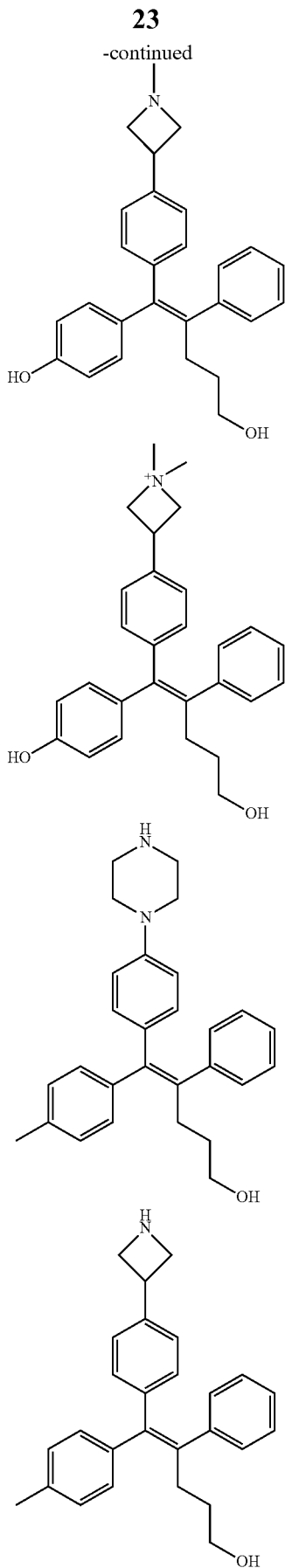
24
-continued
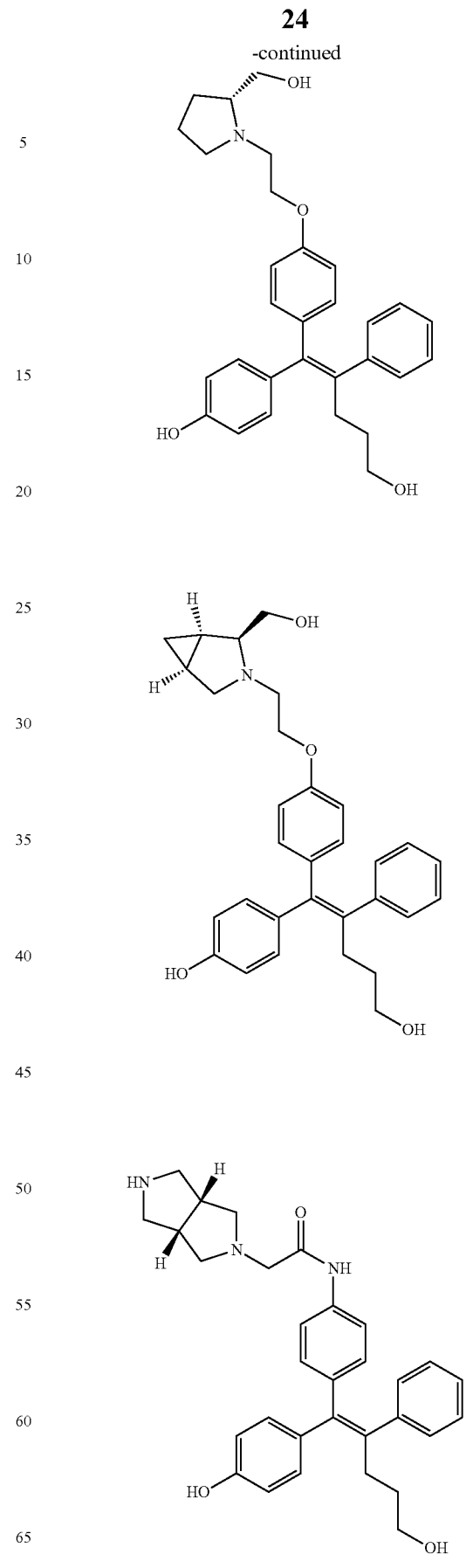

25
-continued
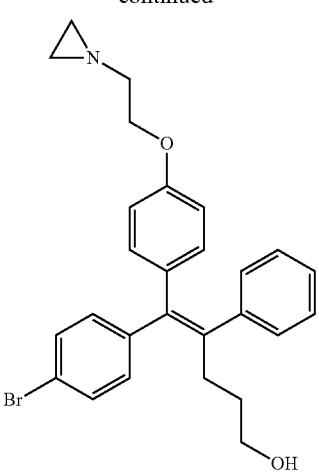
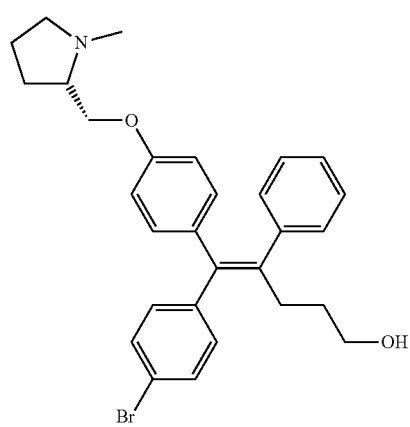
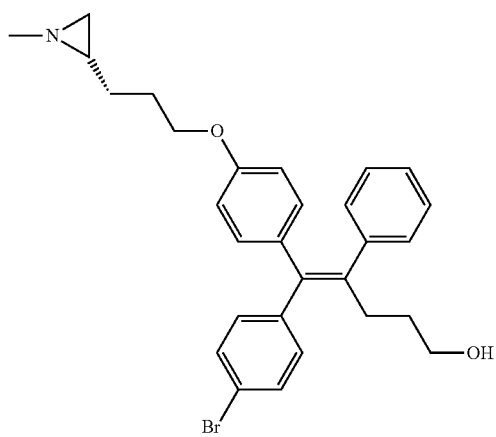
26
-continued
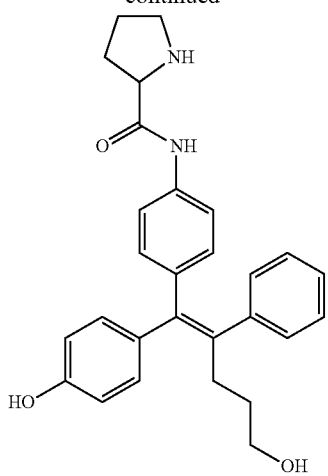
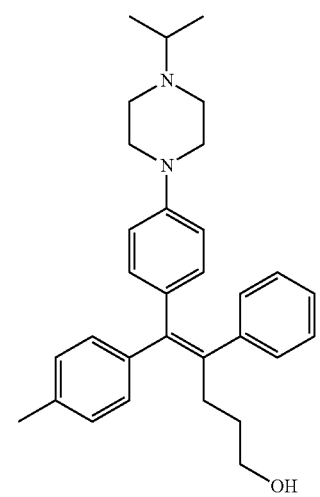
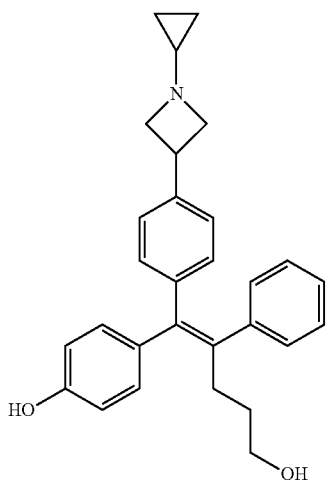

27
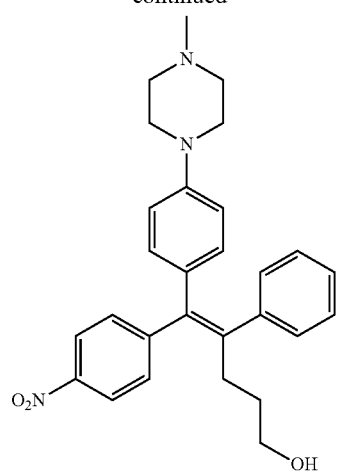
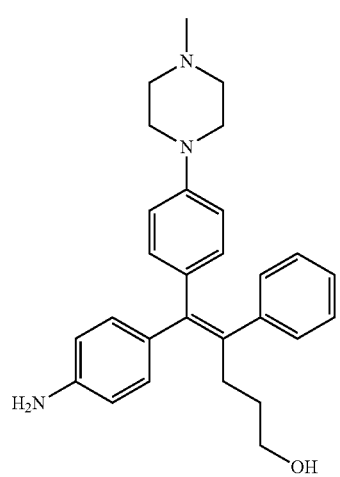
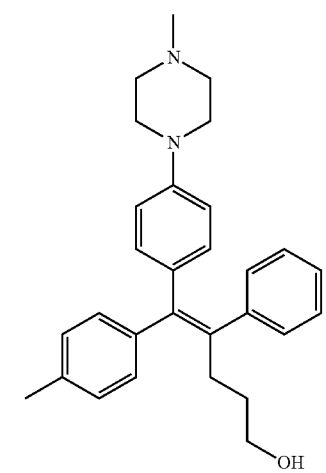
28
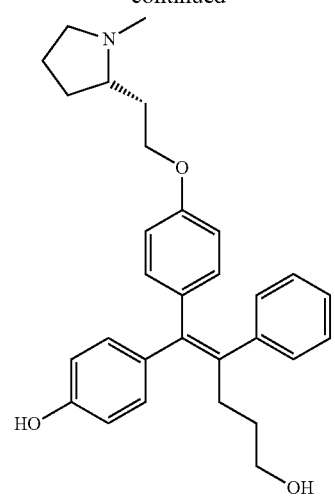
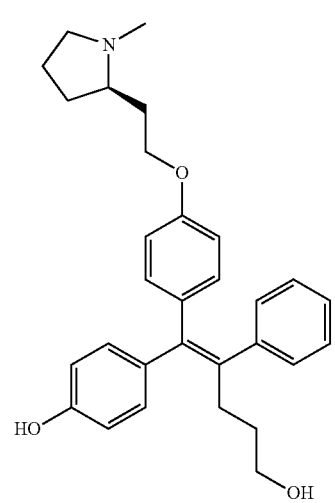
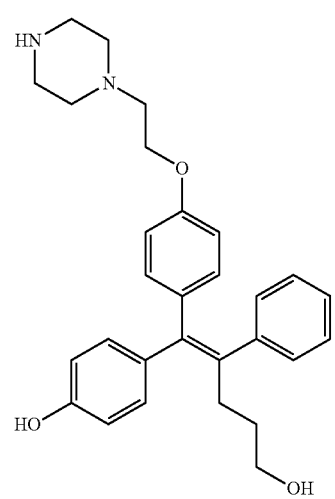

29
-continued
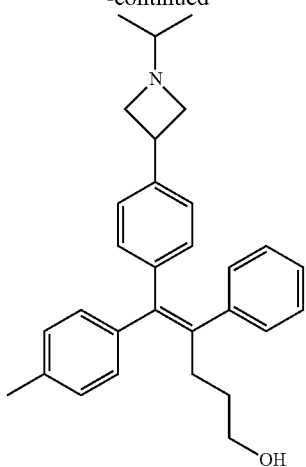
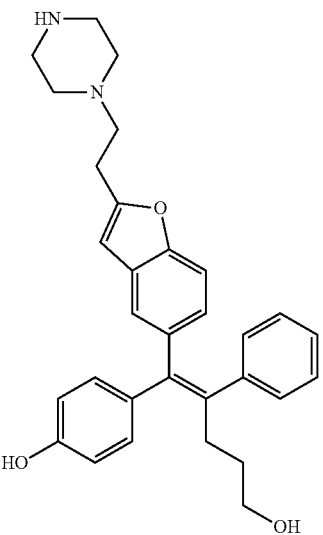
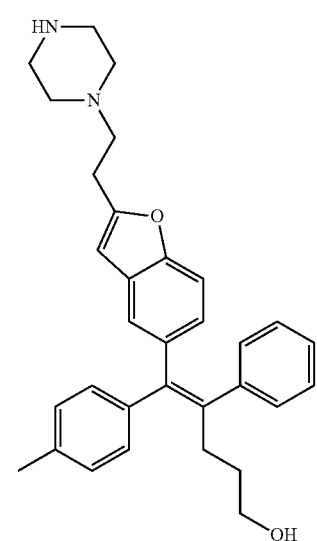
30
-continued
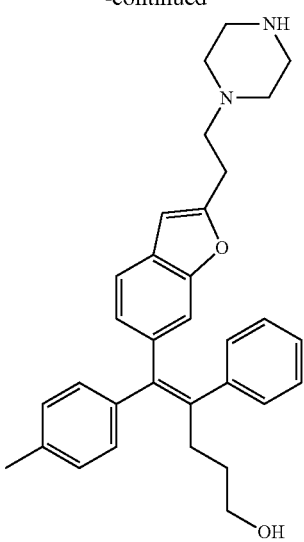
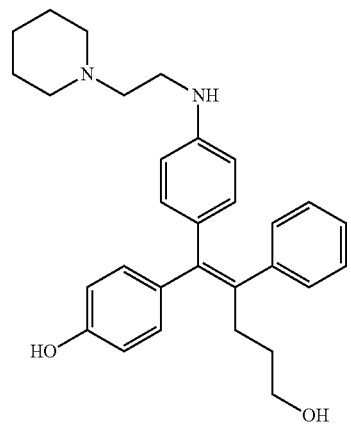
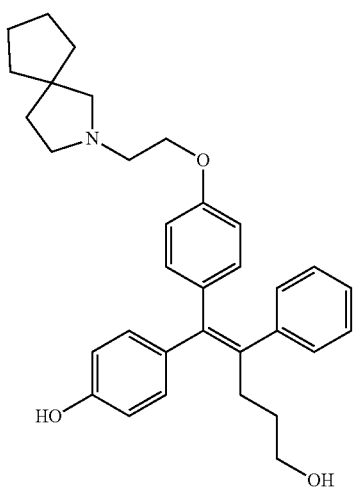

31
-continued
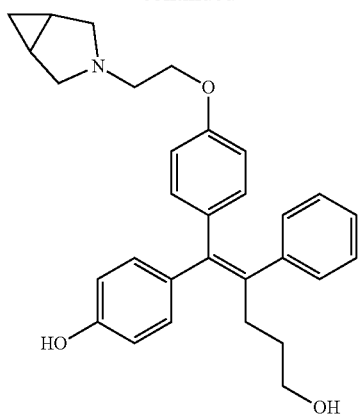
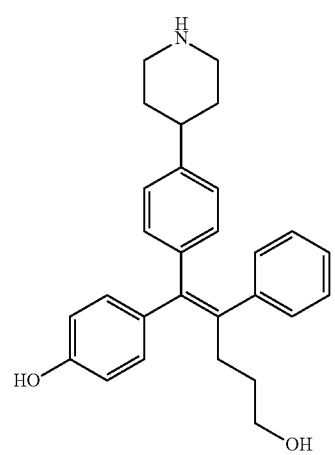
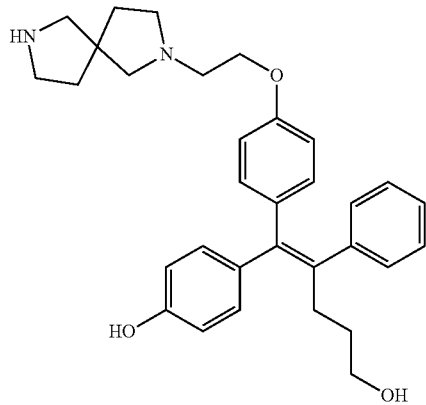
32
-continued
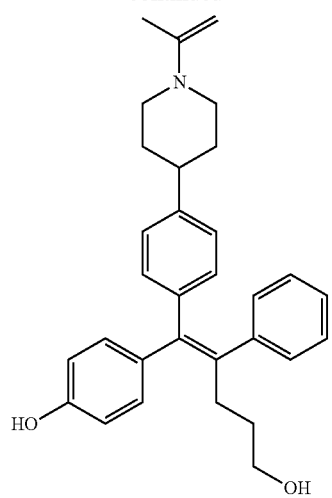
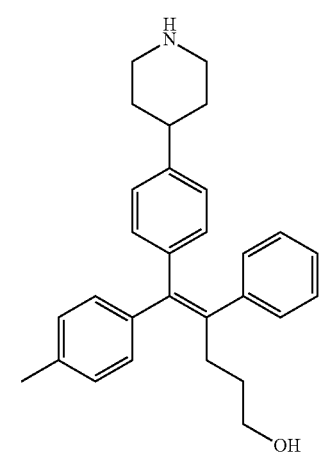
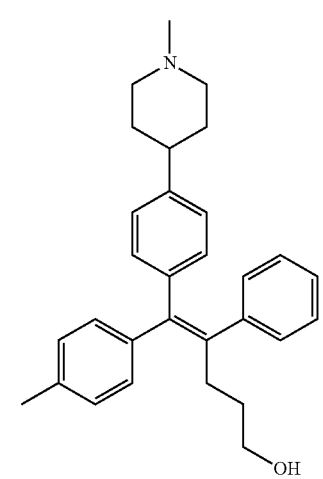

33
-continued
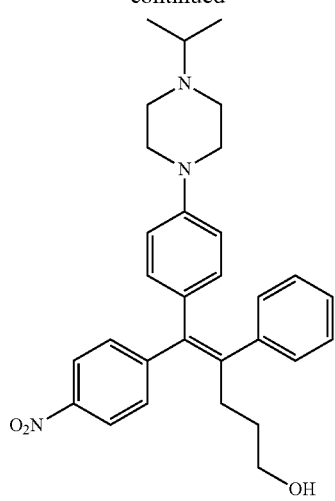
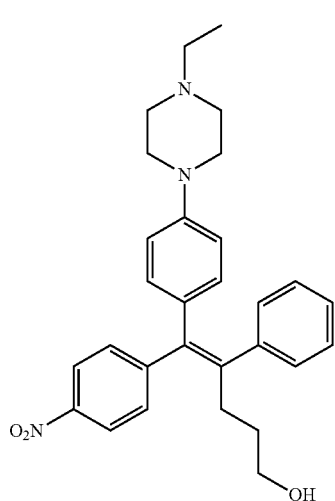
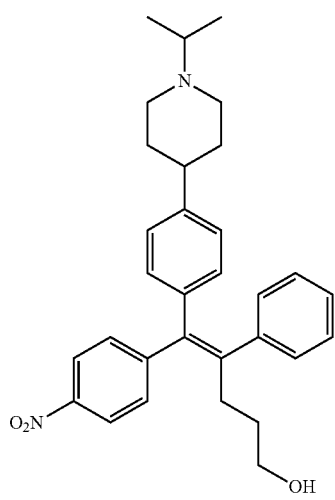
34
-continued
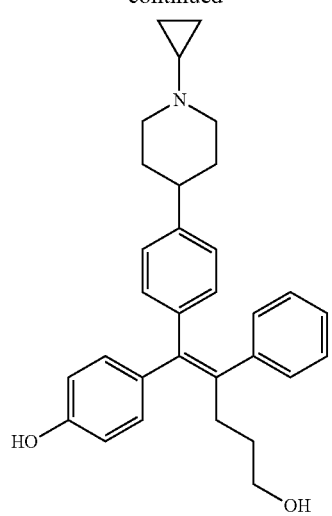
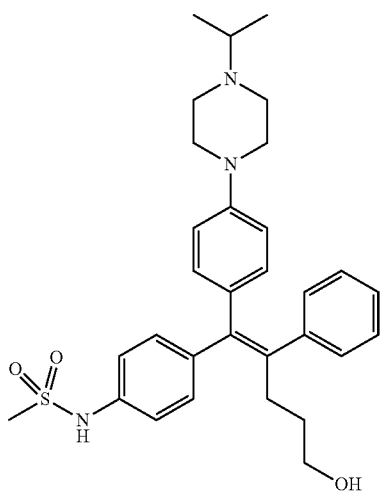
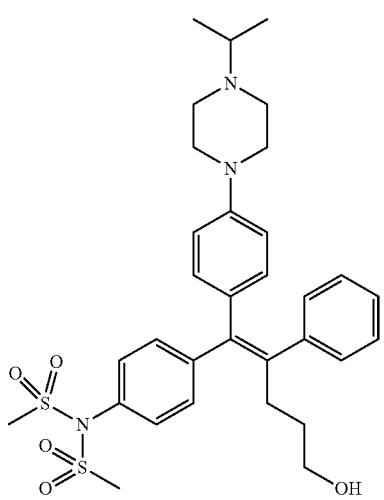

| 35 -continued | 36 -continued |
|---|---|
| 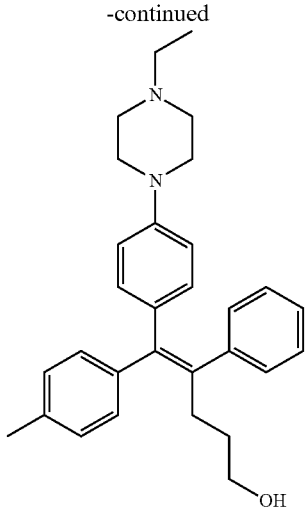 | 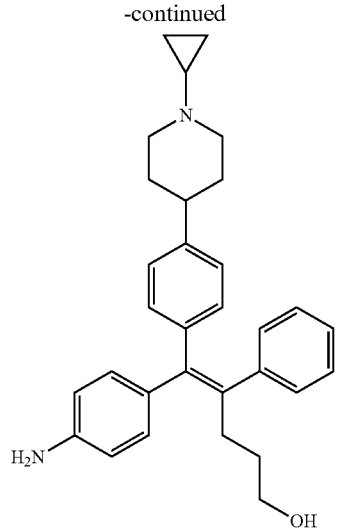 |
| 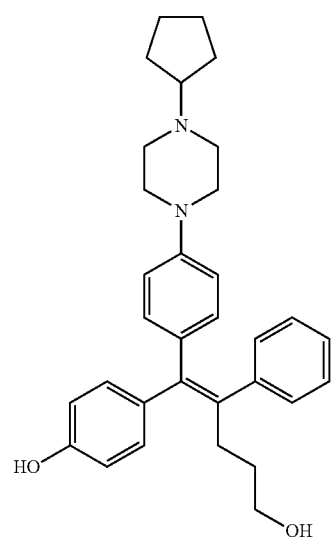 | 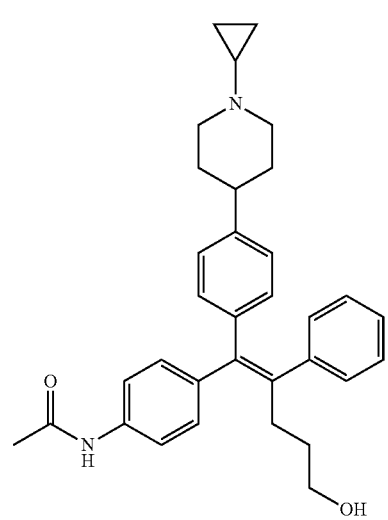 |
| 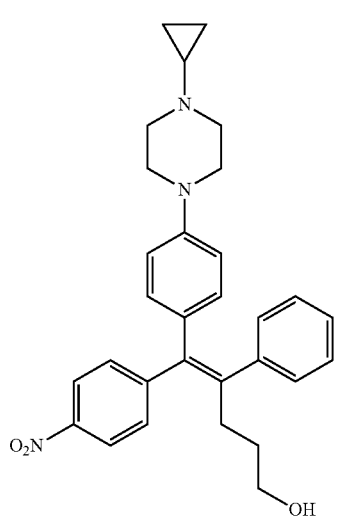 | 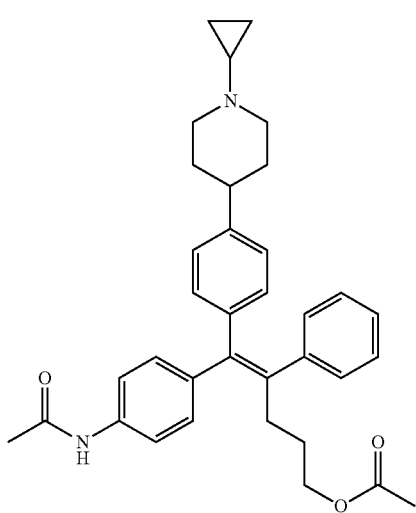 |

37
-continued
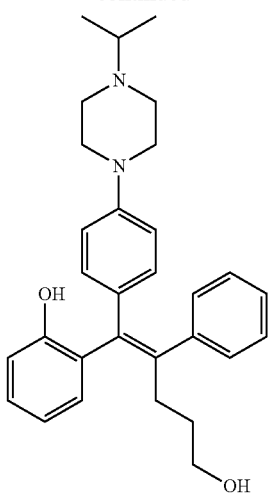
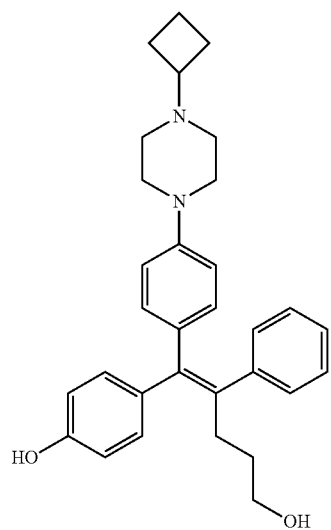
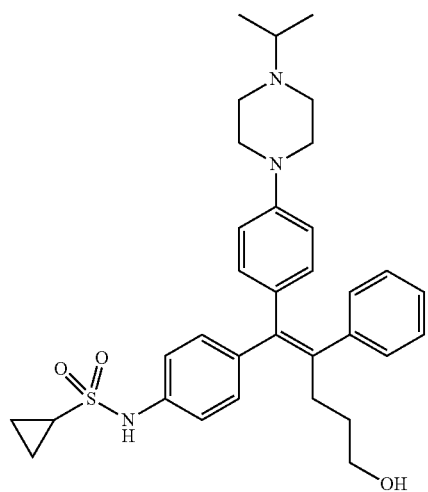
38
-continued
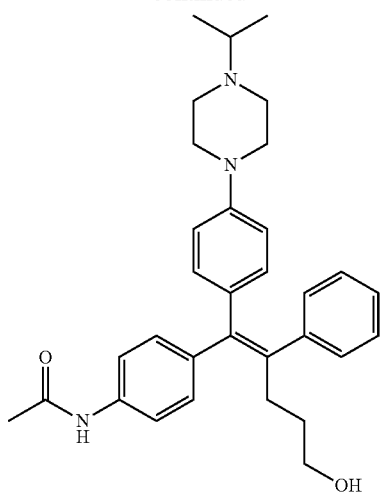
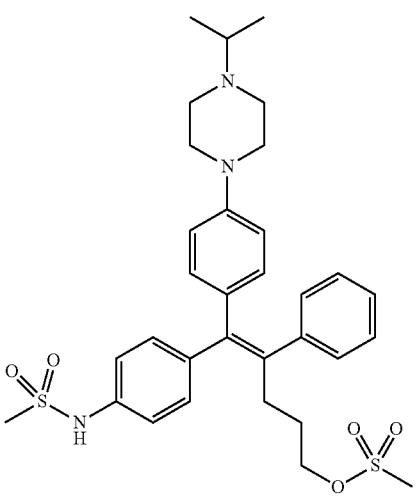
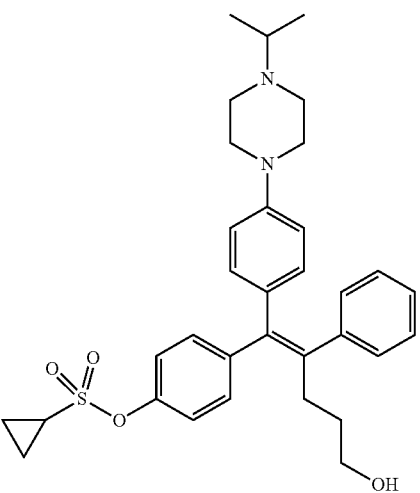

39
-continued
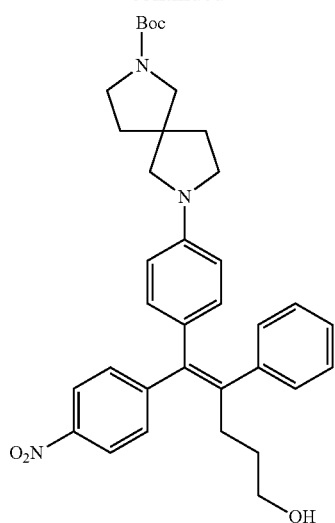
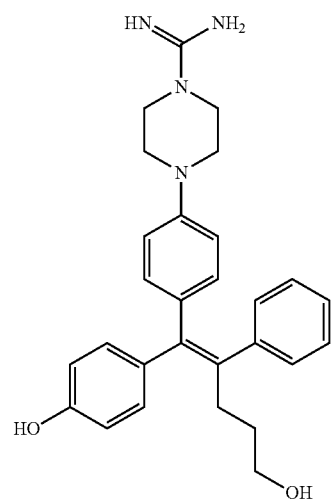
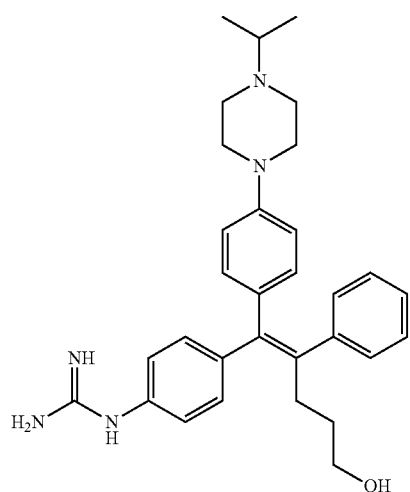
40
-continued
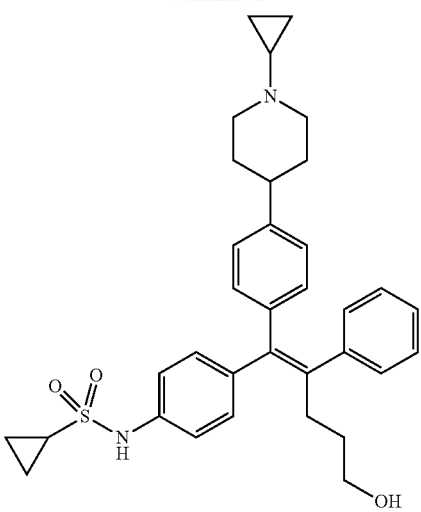
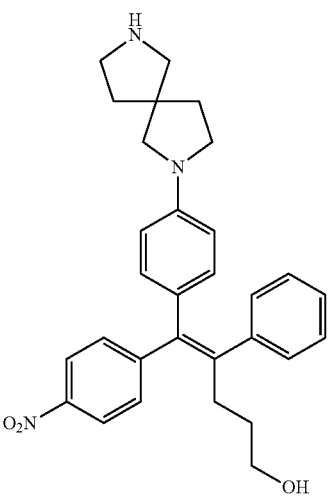
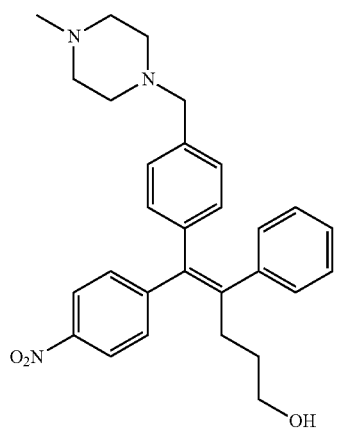

41
-continued
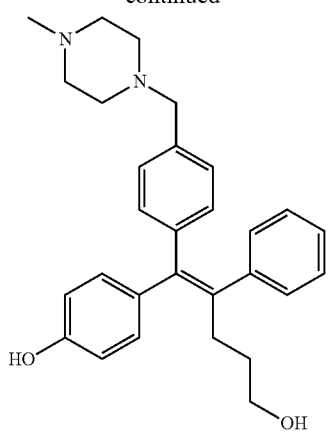
42
-continued
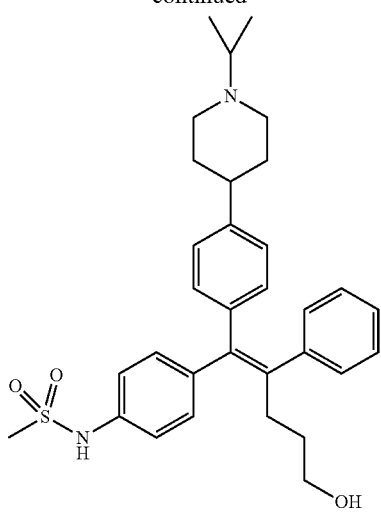
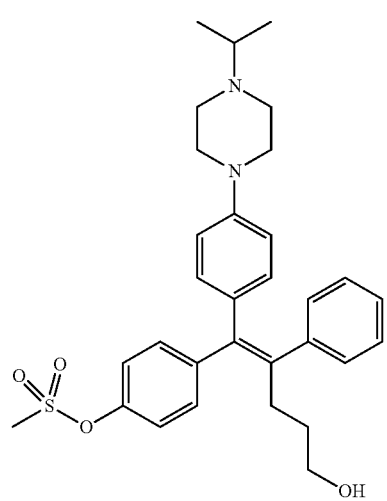
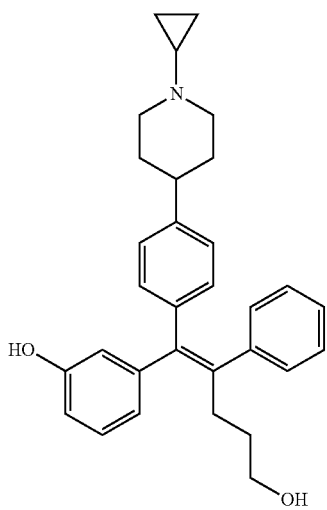
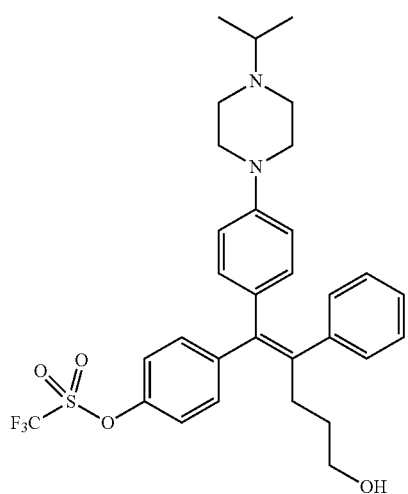
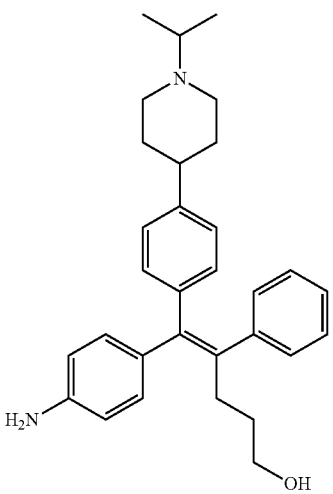

43

44

-continued
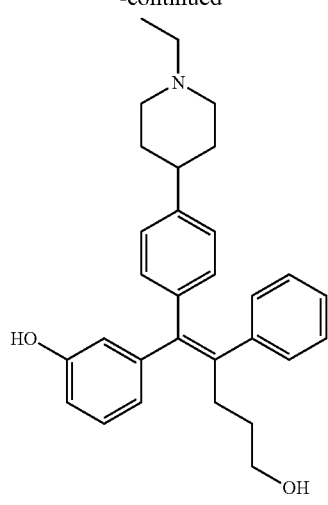
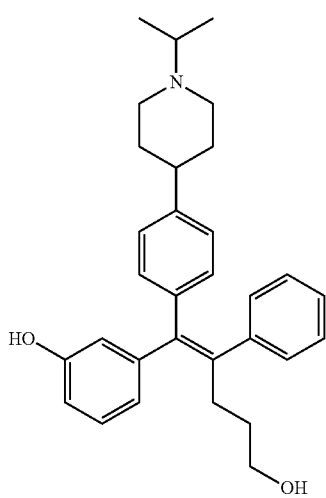
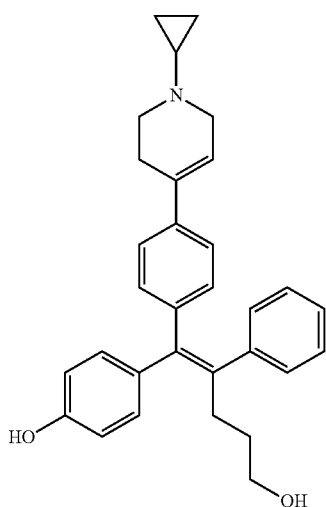
-continued
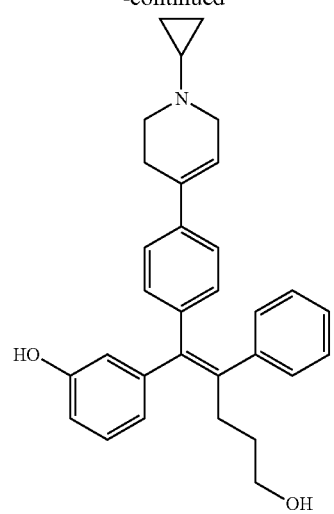
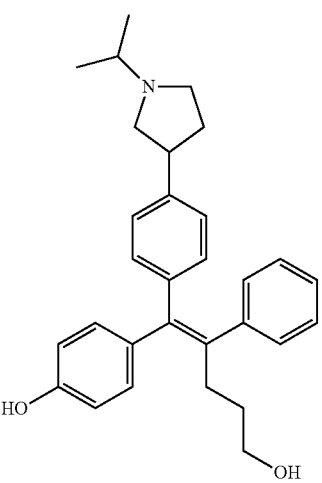
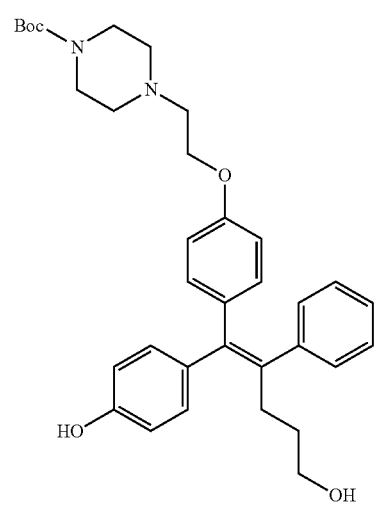

47
-continued
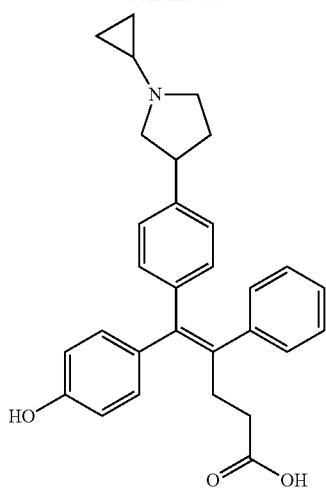
48
-continued
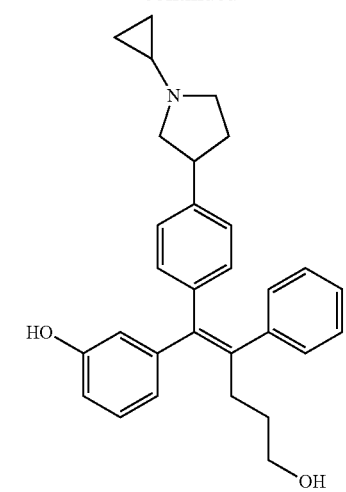
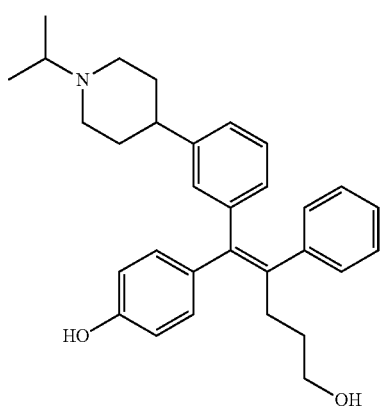
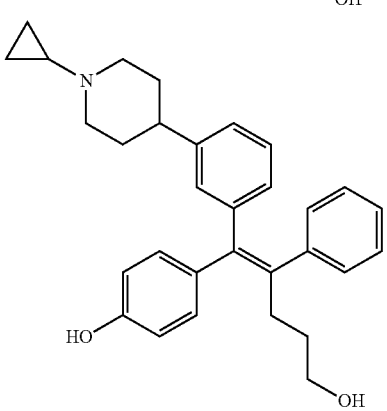
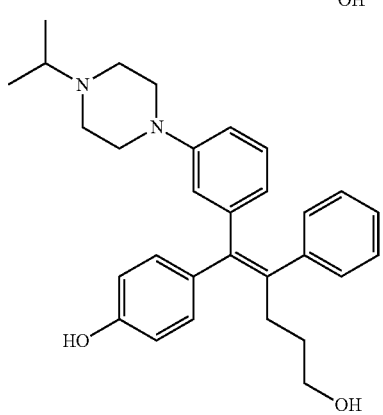

49
-continued
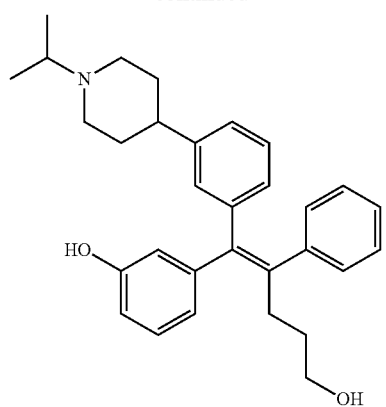
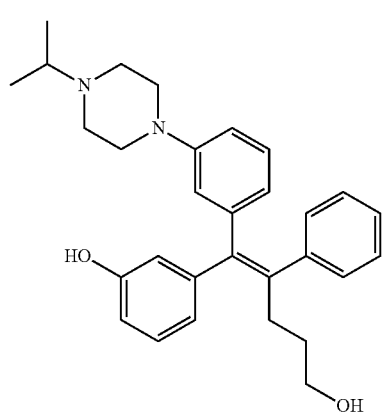
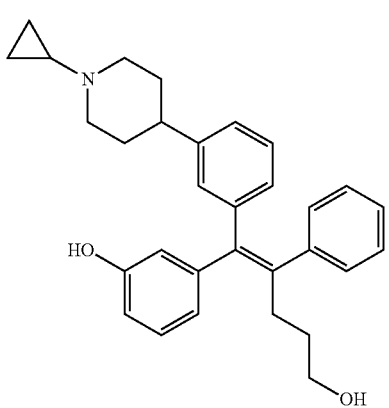
50
-continued
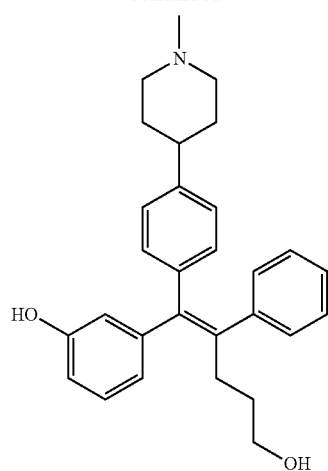
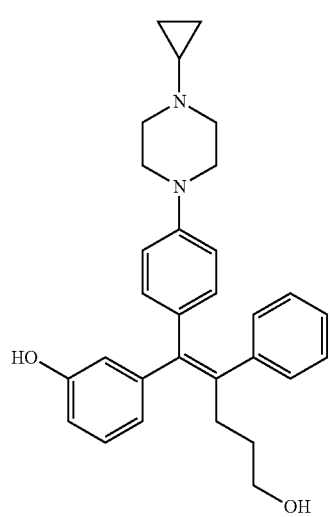
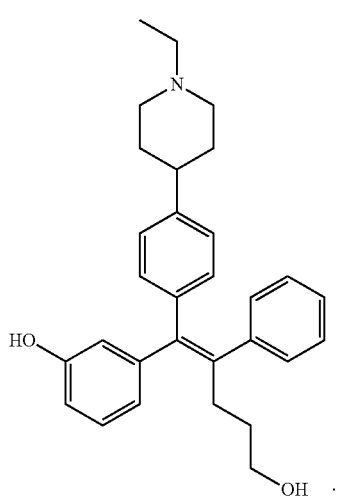

In still another embodiment, the compound of Chemical Formula 1 can be any of the following compounds:

(=DMRC200434)

Compound 18a

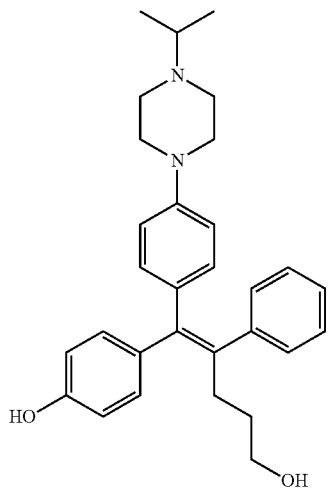

(E)-5-(4-hydroxyphenyl)-5-(4-(4-isopropylpiperazin-1-yl)phenyl)-4-phenylpent-4-en-1-ol (=DMRC2001000)

Compound 18k

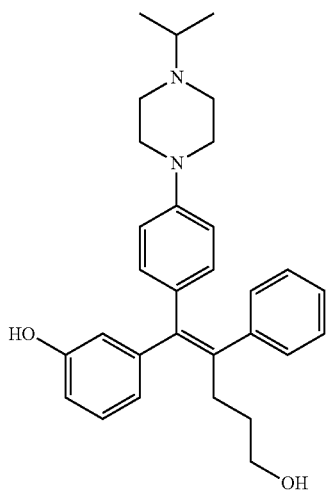

(E)-5-(5-hydroxyphenyl)-5-(4-(4-isopropylpiperazin-1-yl)phenyl)-4-phenylpent-4-en-1-ol (DMRC200699)

Compound 22i

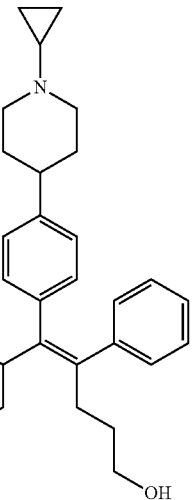

(E)-5-(4-hydroxyphenyl)-5-(4-(N-cyclopropylpiperidin-4-yl)phenyl)-4-phenylpent-4-en-1-ol (DMRC200996)

Compound 22r

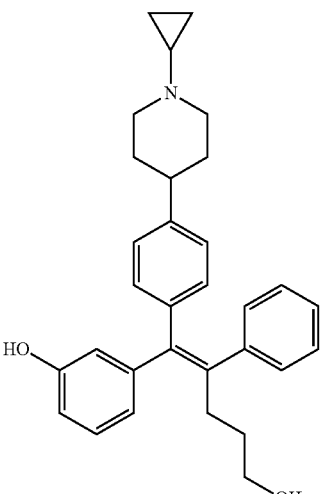

(E)-5-(5-hydroxyphenyl)-5-(4-(N-cyclopropylpiperidin-4-yl)phenyl)-4-phenylpent-4-en-1-ol The pharmaceutical composition according to an embodiment comprises a compound as described above, or a pharmaceutically acceptable salt thereof, or a solvate thereof, or an isomer thereof, as an active ingredient. The pharmaceutical composition may include a pharmaceutically acceptable carrier, excipient, or additive, known in the art.

Methods of Use

In general, the disclosure relates to methods or uses for treating cytokine release syndrome, in particular virulent infection-induced cytokine release syndrome, which comprises administering aryl ethene compounds of Chemical Formula 1 or a pharmaceutically acceptable salt, or a pharmaceutical composition thereof.

The methods of treatment according to an embodiment comprise administering a therapeutically effective amount of a compound of Chemical Formula 1, or a pharmaceutically acceptable salt thereof, or a pharmaceutical composition thereof, to a patient in need thereof.

Individual embodiments include methods of treating cytokine release syndrome by administering a therapeutically effective amount of a compound of Chemical Formula 1, or a pharmaceutically acceptable salt thereof, or a pharmaceutical composition thereof, to a patient in need thereof.

In one embodiment the compounds disclosed herein may be used for treating inflammatory disorders, particularly inflammatory disorders that are mediated by cytokine release, especially a cytokine storm. For example, the compounds disclosed herein may be used for treating inflammatory disorders that underlie numerous human diseases characterized by a highly activated immune system that leads to secretion of large amounts of circulating pro-inflammatory cytokines after infection with virulent pathogens, in response to host cell injury, or related irritants that activate receptors on immune effector cells including T cells, macrophages, or the like. A central feature of these infectious disorders is the burst in cytokine release, i.e. cytokine storm, from pro-inflammatory cells including macrophages, lymphocytes, and polymorphonuclear leukocytes (PMNs).

The cytokine storm may be exaggerated (hypercytokinemia) and results in a fatal immune reaction with constant activation of immune effector cells that produce sustained and supraphysiologic levels of TNFα, IFNb, IL-1b, and IL-6 that leads to profound tissue injury. The compounds disclosed herein may inhibit the release of pro-inflammatory cytokines (e.g., TNFα, IFNb, IL-1b, and/or IL-6).

In certain embodiments, the compounds disclosed herein are panreactive to numerous injurious cytokines. For example, the compounds disclosed herein may inhibit hypercytokinemia, and/or may prevent or diminish supraphysiologic levels of TNFα, IFNb, IL-1b, and/or IL-6 or related injurious molecules.

Inflammatory disorders that may be treated by the compounds disclosed herein include any disorder possessing an inflammatory component. Illustrative inflammatory disorders include acute and chronic inflammation disorders such as asthma, chronic obstructive lung disease, pulmonary fibrosis, pneumonitis (including hypersensitivity pneumonitis and radiation pneumonitis), pneumonia, human immunodeficiency virus related inflammation, sepsis, vasculitis, bursitis, viral or influenza-induced inflammation, or edema. The compounds disclosed herein may be effective for treating sepsis, pneumonia, viral infection-induced inflammation (e.g., influenza-induced inflammation), edema, and the like. The compounds disclosed herein may be useful for treating inflammation and tissue damage induced by pathogenic infection. In an embodiment, pathogenic infection may be a virulent infection. The compounds disclosed herein may be effective for treating sepsis or pneumonia.

Another embodiment disclosed herein is a method for suppressing pro-inflammatory cytokine production in a subject, comprising administering to the subject a compound disclosed herein as an anti-ERRg inhibitor. The pro-inflammatory cytokine includes TNFα, IFNb, IL-1b, and/or IL-6 or related injurious molecules.

Another embodiment disclosed herein is a method for diminishing supraphysiological level of pro-inflammatory cytokine production in a subject, comprising administering to the subject a compound disclosed herein as an anti-ERRg inhibitor. The pro-inflammatory cytokine includes TNFα, IFNb, IL-1b, and/or IL-6 or related injurious molecules.

As used herein, "treat" or "treatment" in reference to a disorder means: (1) to ameliorate the disorder or one or more of the biological manifestations of the disorder, (2) to interfere with (a): one or more points in the biological cascade that leads to or is responsible for the disorder, or (b): one or more of the biological manifestations of the disorder, (3) to alleviate one or more of the symptoms or effects associated with the disorder, or (4) to slow the progression of the disorder or one or more of the biological manifestations of the disorder.

The term "treatment" of a disorder may include prevention or prophylaxis of the disorder. The term "prevention" refers to a prophylactic administration of a drug to substantially diminish the likelihood or severity of a disorder or biological manifestation thereof, or to delay the onset of such disorder or biological manifestation thereof.

The term "effective amount" as used herein in reference to a compound of Chemical Formula 1, or a pharmaceutically acceptable salt thereof, or other pharmaceutically active agent means an amount of the compound sufficient to treat the patient's condition within the scope of sound medical judgment. An effective amount of a compound will vary with the particular compound chosen (for example, the potency, efficacy, and half-life of the compound will be considered); the route of administration chosen; the disorder being treated; the severity of the disorder being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

The term "patient" or "subject" as used herein refers to a human or other mammal. The mammal can be any type of mammal including, without limitation, a mouse, rat, dog, cat, horse, sheep, goat, cow, pig, monkey, or human. In one embodiment, "patient" refers to a human.

An embodiment of the disclosure further provides a method for the treatment of cytokine release syndrome, which method comprises administering to a patient in need thereof an effective amount of a compound of Chemical Formula 1, a pharmaceutically acceptable salt thereof, or a solvate thereof. In one embodiment, cytokine release syndrome is induced by virulent infection. The infection could be an infection by virus or bacteria.

In one embodiment there is provided a method for the treatment, prevention, or management of virulent infection-induced cytokine release syndrome, which method comprises administering to a patient in need thereof a therapeutically effective amount of a compound of Chemical Formula 1, a pharmaceutically acceptable salt thereof, or a solvate thereof.

In one embodiment there is provided a method for the treatment of cytokine release syndrome, which method comprises administering to a patient in need thereof a therapeutically effective amount of (E)-5-(4-hydroxyphenyl)-5-(4-(4-isopropylpiperazin-1-yl)phenyl)-4-phenylpent-4-en-1-ol (Compound DMRC200344 or 18a) or a pharmaceutically acceptable salt thereof or a solvate thereof. In one embodiment, cytokine release syndrome is induced by virulent infection. The infection may be an infection by virus or bacteria.

In another embodiment there is provided a method for the treatment of cytokine release syndrome which method comprises administering to a patient in need thereof a therapeutically effective amount of (E)-5-(5-hydroxyphenyl)-5-(4-(4-isopropylpiperazin-1-yl)phenyl)-4-phenylpent-4-en-1-ol (Compound DMRC2001000 or 18k), a pharmaceutically acceptable salt thereof, or a solvate thereof. In one embodiment, cytokine release syndrome is induced by virulent infection. The infection may be an infection by virus or bacteria.

In another embodiment there is provided a method for the treatment of cytokine release syndrome, which method comprises administering to a patient in need thereof a therapeutically effective amount of (E)-5-(4-hydroxyphenyl)-5-(4-(N-cyclopropylpiperidin-4-yl)phenyl)-4-phenylpent-4-en-1-ol (Compound DMRC200699 or 22i), a pharmaceutically acceptable salt thereof, or a solvate thereof. In one embodiment, cytokine release syndrome is induced by virulent infection. The infection may be an infection by virus or bacteria.

In another embodiment there is provided a method for the treatment of cytokine release syndrome, which method comprises administering to a patient in need thereof a therapeutically effective amount of (E)-5-(5-hydroxyphenyl)-5-(4-(N-cyclopropylpiperidin-4-yl)phenyl)-4-phenylpent-4-en-1-ol (Compound DMRC200699 or 22r), a pharmaceutically acceptable salt thereof, or a solvate. In one embodiment, cytokine release syndrome is induced by virulent infection. The infection may be an infection by virus or bacteria.

In a further aspect, there is provided a compound of Chemical Formula 1, a pharmaceutically acceptable salt thereof, or a solvate thereof for use in reducing cytokine levels in a subject infected by a pathogen. The cytokine level is a serum cytokine level. The cytokine includes, among others, IFNb, IL1b, TNFα, and/or IL6.

In one embodiment there is provided a compound of Chemical Formula 1, a pharmaceutically acceptable salt thereof, or a solvate thereof for use in the treatment of cytokine release syndrome. In one embodiment, cytokine release syndrome is induced by virulent infection. The infection may be an infection by virus or bacteria. The treatment of cytokine release syndrome may include normalizing serum cytokine level of a patient. The cytokine includes, among others, IFNb, IL1b, TNFα, and/or IL6.

In one embodiment there is provided the use of a compound of Chemical Formula 1, a pharmaceutically acceptable salt thereof, or a solvate thereof, in the manufacture of a medicament for use in the treatment of cytokine release syndrome. In one embodiment, cytokine release syndrome is induced by virulent infection. The infection may be an infection by virus or bacteria. The treatment of cytokine release syndrome may include normalizing serum cytokine level of a patient. The cytokine includes, among others, IFNb, IL1b, TNFα, and/or IL6.

In one embodiment there is provided the use of (E)-5-(4-hydroxyphenyl)-5-(4-(4-isopropylpiperazin-1-yl)phenyl)-4-phenylpent-4-en-1-ol (DMRC200344 or 18a), a pharmaceutically acceptable salt thereof, or a solvate thereof, in the manufacture of a medicament for use in the treatment of cytokine release syndrome. In one embodiment, cytokine release syndrome is induced by virulent infection. The infection may be an infection by virus or bacteria. The treatment of cytokine release syndrome may include normalizing serum cytokine level of a patient. The cytokine includes, among others, IFNb, IL1b, TNFα, and/or IL6.

In one embodiment there is provided the use of (E)-5-(5-hydroxyphenyl)-5-(4-(4-isopropylpiperazin-1-yl)phenyl)-4-phenylpent-4-en-1-ol (DMRC2001000 or 18k), a pharmaceutically acceptable salt thereof, or a solvate thereof, in the manufacture of a medicament for use in the treatment of cytokine release syndrome. In one embodiment, cytokine release syndrome is induced by virulent infection. The infection may be an infection by virus or bacteria. The treatment of cytokine release syndrome may include normalizing serum cytokine level of a patient. The cytokine includes, among others, IFNb, IL1b, TNFα, and/or IL6.

In one embodiment there is provided the use of (E)-5-(4-hydroxyphenyl)-5-(4-(N-cyclopropylpiperidin-4-yl)phenyl)-4-phenylpent-4-en-1-ol (DMRC200699 or 22i), a pharmaceutically acceptable salt thereof, or a solvate thereof, in the manufacture of a medicament for use in the treatment of cytokine release syndrome. In one embodiment, cytokine release syndrome is induced by virulent infection. The infection may be an infection by virus or bacteria. The treatment of cytokine release syndrome may include normalizing serum cytokine level of a patient. The cytokine includes, among others, IFNb, IL1b, TNFα, and/or IL6.

In one embodiment there is provided the use of (E)-5-(5-hydroxyphenyl)-5-(4-(N-cyclopropylpiperidin-4-yl)phenyl)-4-phenylpent-4-en-1-ol (DMRC200699 or 22r), a pharmaceutically acceptable salt thereof, or a solvate thereof, in the manufacture of a medicament for use in the treatment of cytokine release syndrome. In one embodiment, cytokine release syndrome is induced by virulent infection. The infection may be an infection by virus or bacteria. The treatment of cytokine release syndrome may include normalizing serum cytokine level of a patient. The cytokine includes, among others, IFNb, IL1b, TNFα, and/or IL6.

In one aspect, the disclosure relates to a method or use for treating cytokine release syndrome, which comprises administering a compound of Chemical Formula 6:

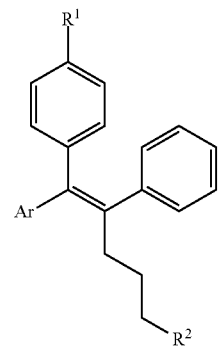

Chemical Formula 6 wherein all the symbols have the same meaning as defined above in Chemical Formula 6,
a pharmaceutically acceptable salt thereof or a solvate thereof to a patient in need thereof. In one embodiment, cytokine release syndrome is induced by virulent infection. The infection may be an infection by virus or bacteria. The treatment of cytokine release syndrome may include normalizing serum cytokine level of a patient. The cytokine includes, among others, IFNb, IL1b, TNFα, and/or IL6.

In another aspect, the present disclosure relates to a method or use for treating cytokine release syndrome, which comprises administering a compound of Chemical Formula 6, wherein $R^2$ is hydroxyl, and $R^1$ is a heterocycloalkyl group selected from the following structures:

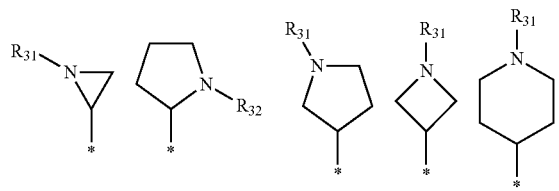

-continued

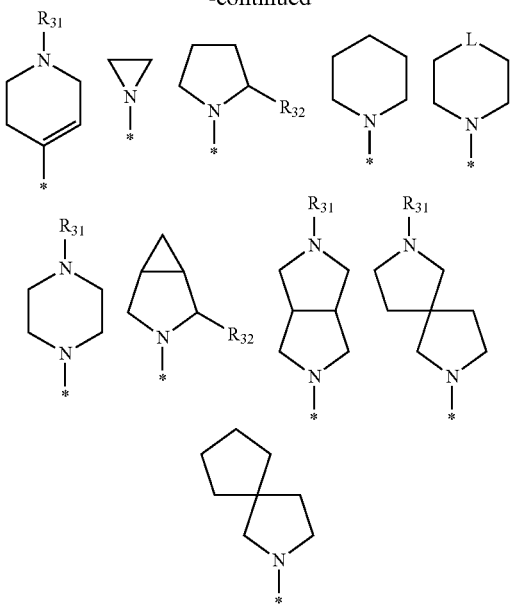

wherein $R^{31}$ and $R^{32}$ are independently hydrogen, (C1-C10)alkyl, (C3-10)cycloalkyl, (C2-C10)alkenyl, amidino, (C1-C10)alkoxycarbonyl, hydroxy(C1-C10)alkyl, or di(C1-C10)alkylamino(C1-C10)alkyl; and L is O or S, a pharmaceutically acceptable salt thereof or a solvate thereof to a patient in need thereof. In one embodiment, cytokine release syndrome is induced by virulent infection. The infection may be an infection by virus or bacteria. The treatment of cytokine release syndrome may include normalizing serum cytokine level of a patient. The cytokine includes, among others, IFNb, IL1b, TNFα, and/or IL6.

In still another aspect, the present disclosure relates to a method or use for treating cytokine release syndrome, which comprises administering a compound selected from the above-listed compounds,
a pharmaceutically acceptable salt thereof, or a solvate thereof, a patient in need thereof. In one embodiment, cytokine release syndrome is induced by virulent infection. The infection may be an infection by virus or bacteria. The treatment of cytokine release syndrome may include normalizing serum cytokine level of a patient. The cytokine includes, among others, IFNb, IL1b, TNFα, and/or IL6.

In still another aspect, the present disclosure relates to a method or use for treating cytokine release syndrome, which comprises administering (E)-5-(4-hydroxyphenyl)-5-(4-(4-isopropylpiperazin-1-yl)phenyl)-4-phenylpent-4-en-1-ol (Compound 18a, DMRC200434),
(E)-5-(5-hydroxyphenyl)-5-(4-(4-isopropylpiperazin-1-yl)phenyl)-4-phenylpent-4-en-1-ol (Compound 18k, DMRC2001000), (E)-5-(4-hydroxyphenyl)-5-(4-(N-cyclopropylpiperidin-4-yl)phenyl)-4-phenylpent-4-en-1-ol (Compound 22i, DMRC200699), or (E)-5-(5-hydroxyphenyl)-5-(4-(N-cyclopropylpiperidin-4-yl)phenyl)-4-phenylpent-4-en-1-ol (Compound 22r, DMRC200996), a pharmaceutically acceptable salt thereof, or a solvate thereof, a patient in need thereof. In one embodiment, cytokine release syndrome is induced by virulent infection. The infection may be an infection by virus or bacteria. The treatment, prevention, or management of cytokine release syndrome may include normalizing serum cytokine level of a patient. The cytokine includes, among others, IFNb, IL1b, TNFα, and/or IL6.

In an aspect, the compound of chemical formula 1 can be administered at a dose ranging from about 0.01 mg/kg body weight to about 1,000 mg/kg body weight, about 0.01 mg/kg to about 500 mg/kg, about 0.01 mg to about 400 mg/kg, about 0.01 mg/kg to 300 mg/kg, about 0.01 mg/kg to 200 mg/kg, about 0.01 mg/kg to about 100 mg/kg, about 0.01 mg/kg to 50 mg/kg, about 0.01 mg/kg to 30 mg/kg, about 0.01 mg/kg to 20 mg/kg, about 0.05 mg/kg body weight to about 1,000 mg/kg body weight, about 0.05 mg/kg to about 500 mg/kg, about 0.05 mg to about 400 mg/kg, about 0.05 mg/kg to 300 mg/kg, about 0.05 mg/kg to 200 mg/kg, about 0.05 mg/kg to about 100 mg/kg, about 0.05 mg/kg to 50 mg/kg, about 0.05 mg/kg to 30 mg/kg, about 0.05 mg/kg to 20 mg/kg, about 0.05 mg/kg to 10 mg/kg, about 0.5 mg/kg to 500 mg/kg, about 0.5 mg/kg to 200 mg/kg, about 0.5 mg/kg to about 100 mg/kg, about 0.5 mg/kg to about 50 mg/kg, about 0.5 mg/kg to about 20 mg/kg, about 0.2 mg/kg to 500 mg/kg, about 0.2 mg/kg to 400 mg/kg, about 0.2 mg/kg to about 300 mg/kg, about 0.2 mg/kg to about 200 mg/kg, about 0.2 mg/kg to about 100 mg/kg, about 0.1 mg/kg to 500 mg/kg, about 0.1 mg/kg to 400 mg/kg, about 0.1 mg/kg to about 300 mg/kg, about 0.1 mg/kg to about 200 mg/kg, about 0.1 mg/kg to about 100 mg/kg, about 0.1 mg/kg to about 50 mg/kg, or about 0.1 mg/kg to about 20 mg/kg.

Compositions

The compounds of the disclosure may, but not necessarily, be formulated into pharmaceutical compositions prior to administration to a patient. Accordingly, in one aspect, there is provided a pharmaceutical composition comprising a compound of formula 1 or a pharmaceutically acceptable salt or solvate thereof and one or more pharmaceutically acceptable excipient or carrier. The pharmaceutical composition, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories.

Suitable pharmaceutically acceptable excipient or carrier will vary depending upon the particular dosage form chosen. In addition, suitable pharmaceutically acceptable excipient or carrier may be chosen for a particular function that they may serve in the composition. For example, certain pharmaceutically acceptable excipient or carrier may be chosen for their ability to facilitate the production of uniform dosage forms. Certain pharmaceutically acceptable excipient or carrier may be chosen for their ability to facilitate the production of stable dosage forms. Certain pharmaceutically acceptable excipient or carrier may be chosen for their ability to facilitate the carrying or transporting of the compound or compounds of formula 1 or pharmaceutically acceptable salts thereof once administered to the patient from one organ, or portion of the body, to another organ, or portion of the body. Certain pharmaceutically acceptable excipient or carrier may be chosen for their ability to enhance patient compliance.

Suitable pharmaceutically acceptable excipient or carrier includes the following types of excipients or carriers: diluents, fillers, binders, disintegrants, lubricants, glidants, granulating agents, coating agents, wetting agents, solvents, co-solvents, suspending agents, emulsifiers, sweeteners, flavouring agents, flavour-masking agents, colouring agents, anti-caking agents, humectants, chelating agents, plasticisers, viscosity increasing agents, antioxidants, preservatives, stabilisers, surfactants, and buffering agents. The skilled artisan will appreciate that certain pharmaceutically acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically acceptable excipient or carrier in appropriate amounts.

The pharmaceutical composition according to an embodiment is prepared using techniques and methods known to those skilled in the art.

The pharmaceutical composition according to an embodiment, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories.

The pharmaceutical composition may contain from 0.1% to 99% by weight, of the active material, depending on the method of administration. The dose of the compound used in the treatment of the aforementioned conditions or disorders will vary in the usual way with the seriousness of the conditions or disorders, the weight of the subject, and other similar factors. However, as a general guide suitable unit doses may be 0.05 to 5000 mg, 1.0 to 500 mg or 1.0 to 200 mg and such unit doses may be administered more than once a day, for example two or three times a day. Such therapy may extend for a number of weeks, months or years.

In one embodiment, the pharmaceutical composition is formulated into injectable or infusible solutions, or reconstitutable powders.

In one embodiment, the pharmaceutical composition is adapted for oral formulation.

Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavorings or colorants, buffer salts and sweetening agents as appropriate. Preparations for oral administration may be suitably formulated to give controlled release of the active compound.

For parenteral administration, fluid unit dosage forms are prepared utilizing a compound of the invention or pharmaceutically acceptable salt thereof and a sterile vehicle. Formulations for injection may be presented in unit dosage form e.g. in ampoules or in multi-dose, utilizing a compound of the invention or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilized before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilizing agents, dispersing agents, suspending agents, thickening agents, or coloring agents. Drops may be formulated with an aqueous or non-aqueous base also comprising one or more dispersing agents, stabilizing agents, solubilizing agents or suspending agents. They may also contain a preservative.

The pharmaceutical composition may also be formulated in rectal compositions such as suppositories or retention enemas, e.g. containing conventional suppository bases such as cocoa butter or other glycerides.

The pharmaceutical composition may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device. Thus compounds of formula (I) may be formulated for oral, buccal, parenteral, topical (including ophthalmic and nasal), depot or rectal administration or in a form suitable for administration by inhalation or insufflation (either through the mouth or nose).

The pharmaceutical composition may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilized components.

An aspect of the disclosure provides for a pharmaceutical composition for use in the treatment, prevention or management of cytokine release syndrome which comprises a compound of formula 1, a pharmaceutically acceptable salt thereof, or a solvate thereof, and one or more pharmaceutically acceptable excipient or carrier. In one embodiment, cytokine release syndrome is induced by virulent infection. The infection may be an infection by virus or bacteria. The treatment, prevention, or management of cytokine release syndrome may include normalizing serum cytokine level of a patient. The cytokine includes, among others, IFNb, IL1b, TNFα, and/or IL6.

REFERENCE PREPARATION EXAMPLE

The compound of chemical formula 1 can be prepared by following the procedure described in U.S. application Ser. No. 16/313,360, of which entire contents are incorporated herein by reference.

Reference Preparation Example 1: Preparation of (E)-5-(4-(2-(aziridin-1-yl)ethoxy)phenyl)-5-(4-bromophenyl)-4-phenylpent-4-en-1-ol hydrochloride salt (Compound 18t)

By employing the following reaction scheme, compound 18t was prepared:

under reduced pressure, and 1.1 g of the desired compound C-1 (58%) was obtained using column chromatography.

Step 2: Preparation of (E)-tert-butyl 3-(4-(5-methoxy-5-oxo-2-phenyl-1-(4-(pivaloyloxy)phenyl)pent-1-en-1-yl)phenyl)azetidin-1-carboxylate (C-2)

tert-Butyl 3-(4-(4,4,5,5-tetramethyl-1,3,2-dioxaboran-2-yl)phenyl)azetidin-1-carboxylate (0.27 g, 0.75 mmol), compound C-1 (0.14 g, 0.5 mmol), and iodobenzene (84 μL, 0.75 mmol) were dissolved in DMF (8 mL) and water (4 mL), 0.025 M PdCl$_2$(PhCN)$_2$ (0.2 mL, 5 μmol) was added thereto, and heating was performed at 45° C. for 10 minutes. Cesium carbonate (0.24 g, 0.75 mmol) was added thereto, and heating was performed at 45° C. for 12 hours. When the reaction was completed, brine and ethyl acetate was further added to the reaction solution, and an organic layer was extracted. The organic layer was dried with anhydrous Na$_2$SO$_4$ and filtered. The solvent was distilled under reduced pressure to obtain a residue, which was purified using column chromatography, thereby obtaining 81 mg of the desired compound C-2 (27%).

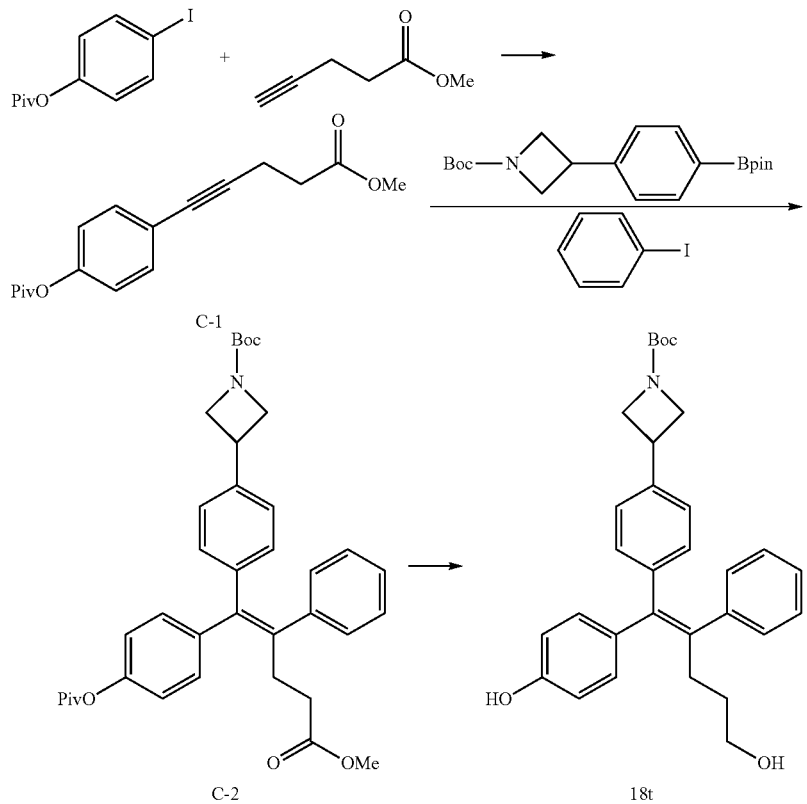

Step 1: Preparation of methyl 5-(4-(pivaloyloxy)phenyl)pent-4-ynoate (C-1)

4-Iodophenyl pivalate (2 g, 6.6 mmol), copper (I) chloride (0.13 g, 0.66 mmol), bis(triphenylphosphine)palladium (II) dichloride (PdCl$_2$(PPh$_3$)$_2$, 0.23 g, 0.33 mmol), and methyl pent-4-ynoate (0.74 g, 0.66 mmol) were dissolved in triethylamine (15 mL), and the reaction was carried out at 50° C. for 12 hours. The reaction solution was concentrated Step 3: Preparation of tert-butyl (E)-3-(4-(5-hydroxy-1-(4-hydroxyphenyl)-2-phenylpent-1-en-1-yl)phenyl)azetidine-1-carboxylate (18t)

Compound C-2 (0.021 mmol) was added to tetrahydrofuran (2 mL), the temperature was lowered to 0° C., and 1 M lithium aluminum hydride, diisobutylaluminum hydride, or lithium borohydride (0.024 mL, 0.024 mmol) was added thereto. The temperature was raised to room temperature, and stirring was performed for 1 hour. Water and ethyl acetate were further added to the reaction solution and an organic layer was extracted. The organic layer was dried with anhydrous $Na_2SO_4$ and filtered. The solvent was distilled under reduced pressure to obtain a residue, which was purified using column chromatography and then dissolved in methanol:dichioromethane (1:1), the temperature was lowered to 0° C., a 1M aqueous HCl solution was slowly added thereto, and distillation under reduced pressure was performed, thereby obtaining 24 mg of the desired compound 18t (78%).

Reference Preparation Examples 2-3

Compounds 18a and 18t were prepared using the process of Reference Preparation Example 1. Identification data of the thus-prepared compounds 18a and 18t is shown in the following Table 1.

TABLE 1

| Example | Cmpd No. | X-[phenyl]- | R | Identification data |
|---|---|---|---|---|
| 1 | 18t | 4-HO-phenyl | Boc-azetidinyl-(4-phenyl)- | $^1$H-NMR (CD$_3$OD, 400 MHz) δ 7.18-7.10 (m, 5H), 7.05 (d, J = 8.4 Hz, 2H), 6.98 (d, J = 8.2 Hz, 2H), 6.88 (d, J = 8.2 Hz, 2H), 6.79 (d, J = 8.4 Hz, 2H), 4.25 (t, J = 8.4 Hz, 2H), 3.81 (t, J = 6.6 Hz, 2H), 3.66 (m, 1H), 3.43 (t, J = 6.8 Hz, 2H), 2.55 (m, 2H), 1.57 (m, 2H), 1.45 (s, 9H). MS (ESI) m/z: 386 [M + H]$^+$. |
| 2 | 18a | 4-HO-phenyl | iPr-piperazinyl-(4-phenyl)- | $^1$H-NMR (CD$_3$OD, 400 MHz) δ 7.14-7.07 (m, 5H), 7.02 (d, J = 8.0 Hz, 2H), 6.78 (m, 4H), 6.69 (d, J = 8.3 Hz, 2H), 3.76 (m, 2H), 3.52 (m, 3H), 3.41 (t, J = 6.4 Hz, 2H), 3.23 (m, 2H), 2.96 (m, 2H), 2.51 (m, 2H), 1.53 (m, 2H), 1.39 (d, J = 6.5 Hz, 6H). MS (ESI) m/z: 457 [M + H]$^+$. |

TABLE 1-continued

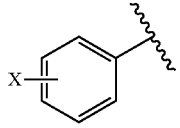

| Example | Cmpd No. | X—⌬— | R | Identification data |
|---|---|---|---|---|
| 3 | 18k | HO—⌬— | [1-(4-phenyl)piperazin-4-yl with isopropyl] | ¹H-NMR (CD₃OD, 400 MHz) δ 7.19-7.09 (m, 6H), 6.81 (d, J = 87 Hz, 2H), 6.69 (m, 4H), 6.63 (m, 1H), 3.76 (m, 2H), 3.53 (m, 3H), 3.40 (t, J = 5.6 Hz, 2H), 3.21 (m, 2H), 2.91 (m, 2H), 2.50 (m, 2H), 1.53 (m, 2H), 1.38 (d, J = 6.6 Hz, 6H). MS (ESI) m/z: 457 [M + H]⁺. |

Reference Preparation Example 4

Preparation of (E)-4-(5-hydroxy-1-(4-(1-isopropylazetidin-3-yl)phenyl)-2-phenylpent-1-en-1-yl)phenol (Compound 22a)

By employing the following reaction scheme, compound 22a was prepared:

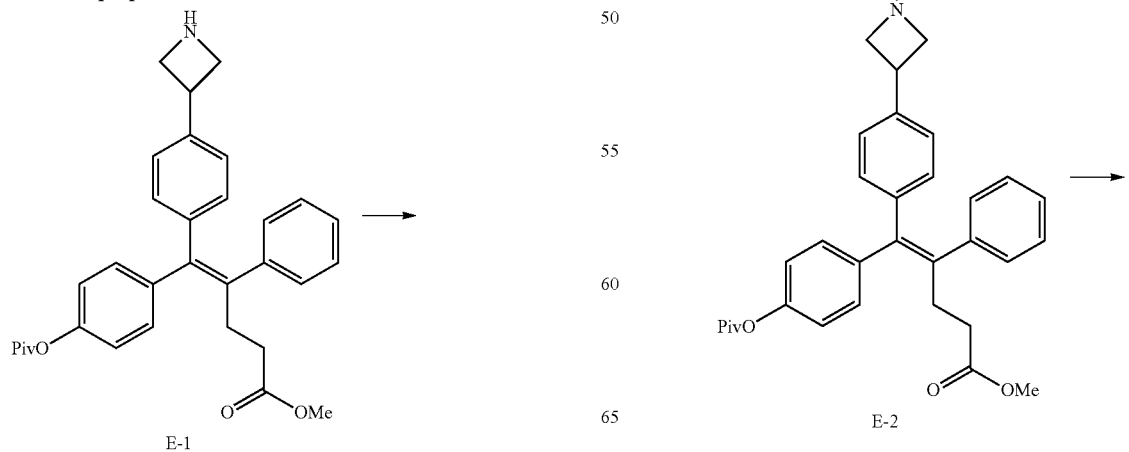

-continued

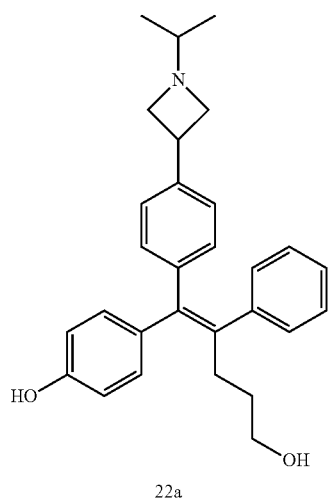

22a

Step 1: Preparation of methyl (E)-5-(4-(1-isopropy-lazetidin-3-yl)phenyl)-4-phenyl-5-(4-(pivaloyloxy)phenyl)pent-4-enoate (E-2)

Compound E-1 (0.03 g, 0.06 mmol), acetone (0.14 mL, 1.9 mmol), and sodium triacetoxyborohydride (NaBH(OAc)$_3$, 41 mg, 0.19 mmol) were added to dichloroethane (3 mL), and stirred at room temperature for 1 hour. Water and ethyl acetate were further added to the reaction solution and an organic layer was extracted. The organic layer was dried with anhydrous Na$_2$SO$_4$ and filtered. The solvent was distilled under reduced pressure to obtain a residue, which was purified using column chromatography, thereby obtaining 18 mg of the desired compound E-2 (54%).

Step 2: Preparation of (E)-4-(5-hydroxy-1-(4-(1-isopropylazetidin-3-yl)phenyl)-2-phenylpent-1-en-1-yl)phenol (22a)

4 mg of the desired compound 22a (27%) was obtained by the same process as step 3 of Example 4, using compound E-2.

Reference Preparation Examples 5-6

Compounds 22i and 22r e were prepared, using the process of Reference Preparation Example 4. Identification data of the thus-prepared compounds 22i and 22r is shown in the following Table 2.

TABLE 3

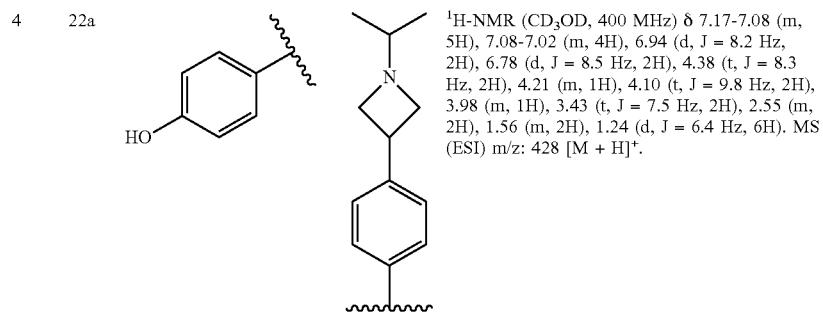

| Example | Cmpd No. | X–⟨phenyl⟩– | R | Identification data |
|---|---|---|---|---|
| 4 | 22a | HO–⟨phenyl⟩– | isopropyl-azetidin-phenyl | $^1$H-NMR (CD$_3$OD, 400 MHz) δ 7.17-7.08 (m, 5H), 7.08-7.02 (m, 4H), 6.94 (d, J = 8.2 Hz, 2H), 6.78 (d, J = 8.5 Hz, 2H), 4.38 (t, J = 8.3 Hz, 2H), 4.21 (m, 1H), 4.10 (t, J = 9.8 Hz, 2H), 3.98 (m, 1H), 3.43 (t, J = 7.5 Hz, 2H), 2.55 (m, 2H), 1.56 (m, 2H), 1.24 (d, J = 6.4 Hz, 6H). MS (ESI) m/z: 428 [M + H]$^+$. |

TABLE 3-continued

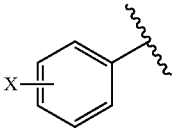

| Example | Cmpd No. | X | R | Identification data |
|---|---|---|---|---|
| 5 | 22i | 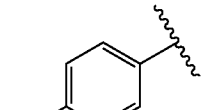 | 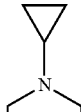 | 1H-NMR (CD3OD, 400 MHz) δ 7.15-7.06 (m, 5H), 7.01 (d, J = 8.4 Hz, 2H), 6.90 (d, J = 8.2 Hz, 2H), 6.84 (d, J = 8.2 Hz, 2H), 6.75 (d, J = 8.5 Hz, 2H), 3.68 (m, 2H), 3.41 (t, J = 6.6 Hz, 2H), 3.24 (m, 2H), 2.79 (m, 2H), 2.52 (m, 2H), 2.02 (m, 2H), 1.78 (m, 2H), 1.54 (m, 2H), 0.97 (m, 4H). MS (ESI) m/z: 454 [M + H]+. |
| 6 | 22r | 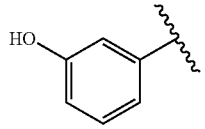 [SMILES: *c1cccc(O)c1] | 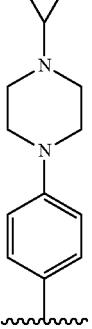 | $^1$H-NMR (CD$_3$OD, 400 MHz) δ 7.21-7.10 (m, 7H), 6.90 (m, 4H), 6.72 (d, J = 7.9 Hz, 2H), 3.71 (m, 2H), 3.43 (t, J = 6.8 Hz, 2H), 3.27 (m, 2H), 2.80 (m, 2H), 2.52 (m, 2H), 2.01 (m, 2H), 1.79 (m, 2H), 1.52 (m, 2H), 0.98 (m, 4H). MS (ESI) m/z: 454 [M + H]$^+$. |

BIOLOGICAL EXAMPLES

Animal Models.

6 to 8-week female C57BL/6 mice (Jackson Lab) were used according to an animal protocol approved by the Institutional Animal Care and Use Committee of Kyungpook National University.

Biological Example 1: Anti-Inflammatory Effect of Compound of Formula 1 on Macrophage Dysregulation of immune activation in innate immune cell is the main factor initiating cytokine release syndrome. Immune regulatory effects of the compound of Chemical Formula 1 on macrophage were assessed employing compound 18a (DMRC200434). 5 μM DMRC200434 was treated on activated macrophage with 100 ng/mL lipopolysaccharide (LPS) (Sigma-Aldrich). 24 hours after LPS treatment, activation markers (CD40, CD80, CD86) were measured by flow cytometry.

Figure 1B:
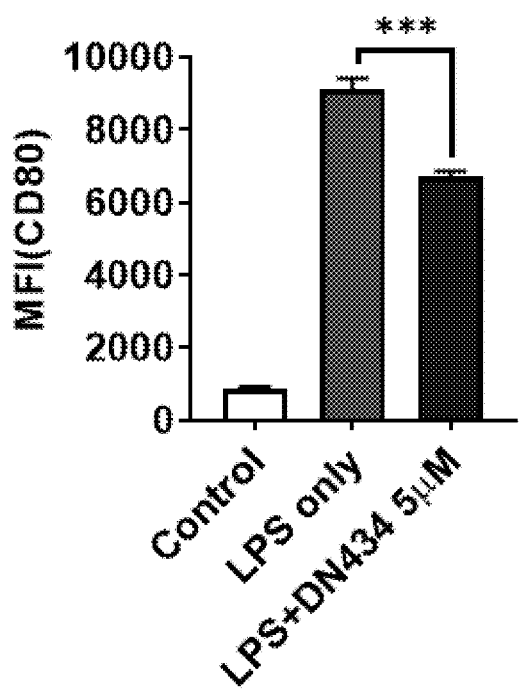
Figure 1C:
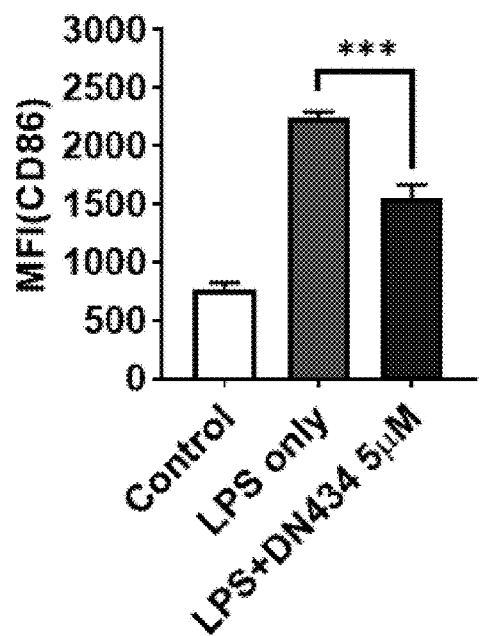

When LPS was triggered on macrophage, inflammatory surface markers (CD40, CD80, CD86) were upregulated, and their expression was downregulated upon a compound of Formula 1 treatment (FIGS. 1A-1C). This result indicate DMRC200434 can potentially treat cytokine release syndrome.

Biological Example 2: LPS Induced Endotoxemia Model

Compound of Chemical Formula 1 (DMRC200434, 30 mg/kg) was dissolved in a solution of 5%—DMSO: 95%—20% PEG400(Saline) and was injected at two points—at 24 hours prior to, and at the start of LPS (50 mg/kg) injection. The survival was observed for 50 hours after LPS injection.

Figure 2:
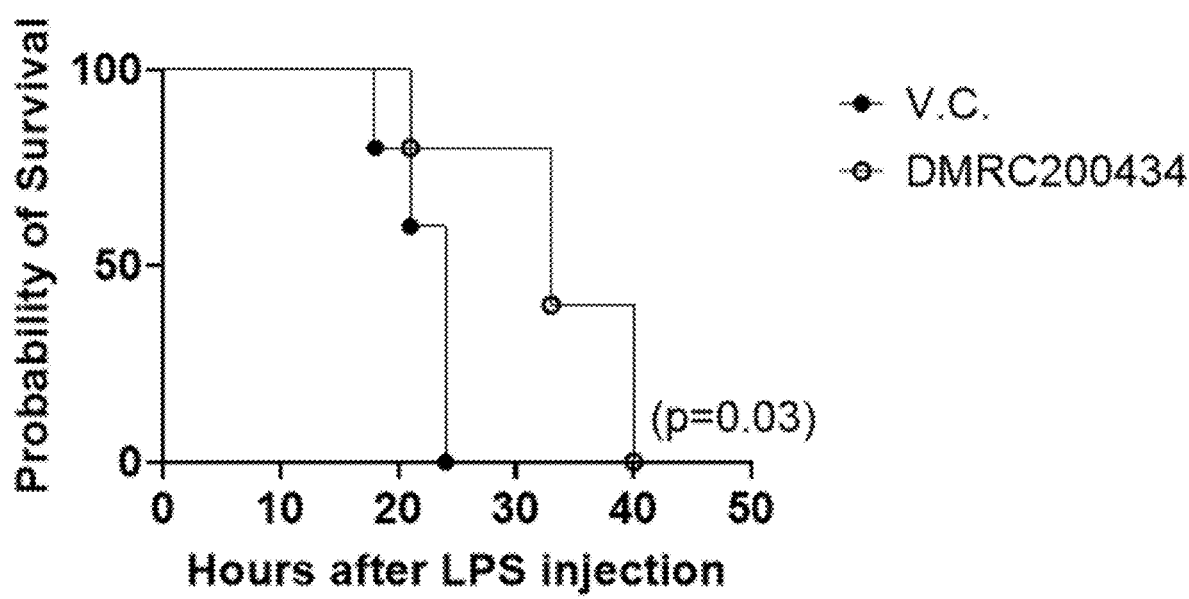
FIG. 2 shows efficacy of a compound of Chemical Formula 1 in vivo on LPS induced endotoxemia model. To assess the effect of a compound of Chemical Formula 1 on endotoxemia LPS induced endotoxemia model, and DMRC200434 was treated on LPS induced endotoxemia model, which resulted in significant delay of endotoxin mediated death. This result indicate a compound of Chemical Formula 1 can treat cytokine release syndrome.

The inventors analyzed the efficacy of a compound of Chemical Formula 1 in vivo on LPS-induced endotoxemia model employing DMRC200434. To assess the effect of DMRC200434 on endotoxemia, DMRC200434 was treated on LPS induced endotoxemia model. DMRC200434 significantly delayed endotoxin mediated death (FIG. 2). This result indicate DMRC200434 can potentially treat cytokine release syndrome.

In view of the many possible embodiments to which the principles of the disclosed invention may be applied, it should be recognized that the illustrated embodiments are only preferred examples of the invention and should not be taken as limiting the scope of the invention.

What is claimed is:

1. A method for treating or managing cytokine release syndrome in a subject in need thereof, comprising administering to the subject an effective amount of a compound selected from the following compounds:

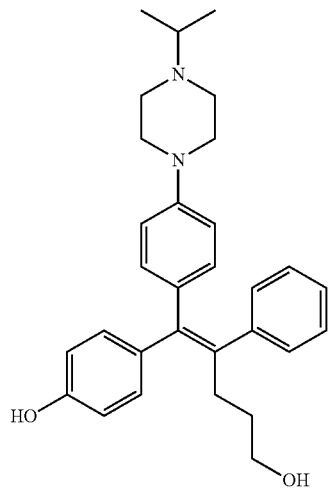

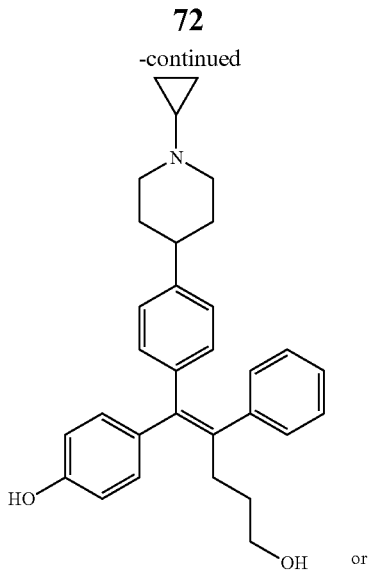

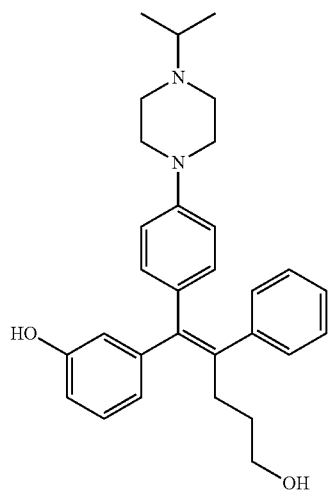

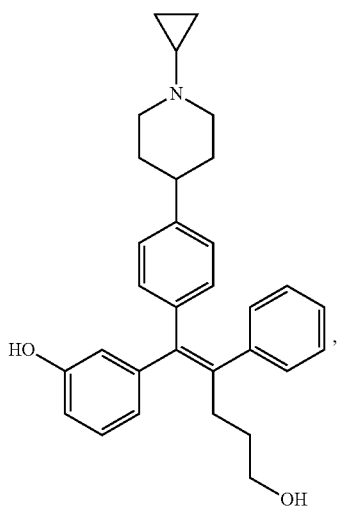 [SMILES: OCCC/C(=C(/c1ccc(C2CCN(C3CC3)CC2)cc1)c1cccc(O)c1)c1ccccc1]

or an isomer, a pharmaceutically acceptable salt thereof, or a solvate thereof, wherein the cytokine release syndrome is caused by an acute inflammatory disorder or virulent infection, and wherein the treating or managing cytokine release syndrome comprises reducing a level of a cytokine in serum of the subject.

2. The method of claim 1, wherein the infection is a viral infection.

3. The method of claim 1, wherein the inflammatory disorder is sepsis.

4. The method claim 1, wherein the inflammatory disorder is pneumonia.

5. The method of claim 1, wherein the cytokine is IFNb, IL1b, TNFa, and/or IL6.

6. The method of claim 1, wherein the compound is (E)-5-(4-hydroxyphenyl)-5-(4-(4-isopropylpiperazin-1-yl)phenyl)-4-phenylpent-4-en-1-ol of the following chemical formula:

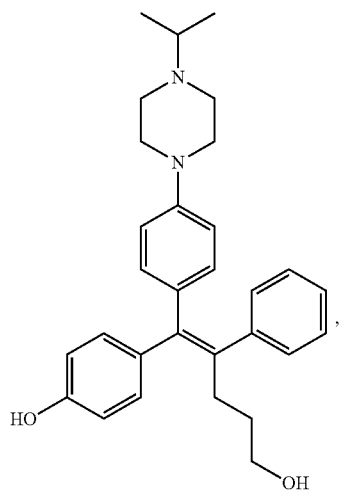

, or an isomer, a pharmaceutically acceptable salt, or a solvate thereof.

7. The method of claim 6, wherein the cytokine release syndrome is induced by viral infection.

8. A method for diminishing supraphysiological levels of one or more selected from the group consisting of IFNb, IL1b, TNFa, and IL6 in a subject in need thereof, comprising administering to the subject an effective amount of a compound selected from the following compounds:

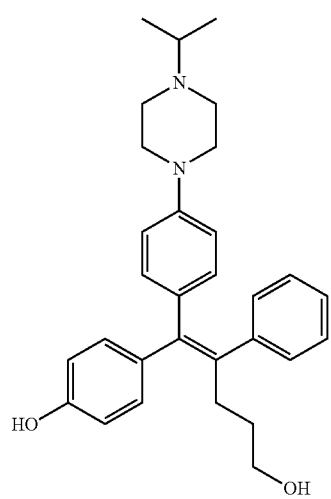

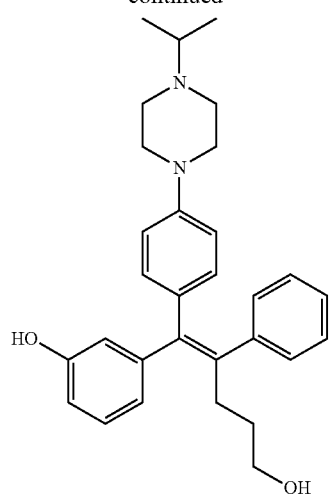

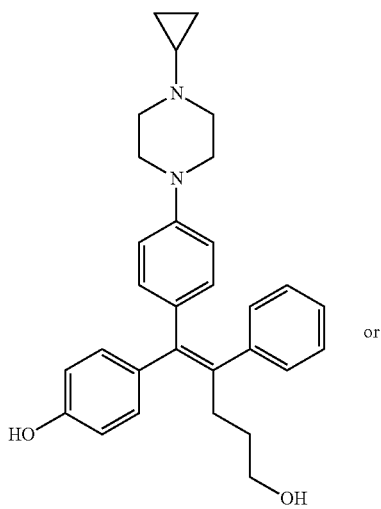 or

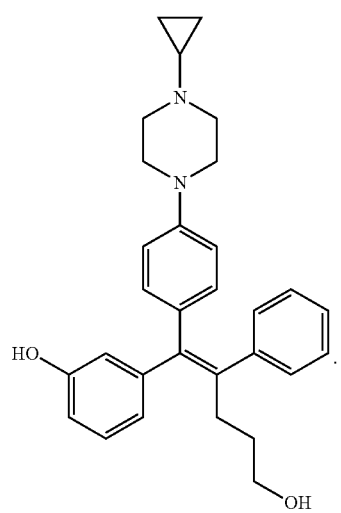 [SMILES: OCCC/C(=C(/c1ccc(N2CCN(C3CC3)CC2)cc1)c1cccc(O)c1)c1ccccc1]

or an isomer, a pharmaceutically acceptable salt thereof, or a solvate thereof, wherein the subject suffers from a virulent infection or acute inflammatory disorder.

9. The method of claim 8, wherein the compound of Chemical Formula 1 is (E)-5-(4-hydroxyphenyl)-5-(4-(4-isopropylpiperazin-1-yl)phenyl)-4-phenylpent-4-en-1-ol of the following chemical formula:
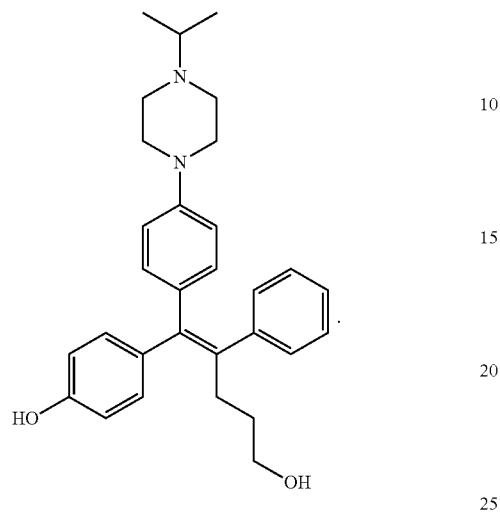
* * * * *